US010325457B2

(12) United States Patent
Saito

(10) Patent No.: US 10,325,457 B2
(45) Date of Patent: Jun. 18, 2019

(54) WRISTBAND-TYPE INFORMATION PROCESSING DEVICE, INFORMATION PROCESSING SYSTEM, AND INFORMATION PROCESSING METHOD

(71) Applicant: SONY CORPORATION, Tokyo (JP)

(72) Inventor: Hiroshi Saito, Tokyo (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 14/912,025

(22) PCT Filed: Jun. 27, 2014

(86) PCT No.: PCT/JP2014/067113
§ 371 (c)(1),
(2) Date: Feb. 12, 2016

(87) PCT Pub. No.: WO2015/029573
PCT Pub. Date: Mar. 5, 2015

(65) Prior Publication Data
US 2016/0196726 A1 Jul. 7, 2016

(30) Foreign Application Priority Data

Aug. 29, 2013 (JP) .................................. 2013-177711

(51) Int. Cl.
*G08B 6/00* (2006.01)
*G06F 1/16* (2006.01)
(Continued)

(52) U.S. Cl.
CPC .............. *G08B 6/00* (2013.01); *A61B 5/1123* (2013.01); *A61B 5/165* (2013.01); *A61B 5/681* (2013.01);
(Continued)

(58) Field of Classification Search
None
See application file for complete search history.

(56) References Cited

U.S. PATENT DOCUMENTS 6,212,427 B1 4/2001 Hoover
2004/0183674 A1* 9/2004 Ruvarac ............. G08B 21/0266
340/539.13
(Continued)

FOREIGN PATENT DOCUMENTS

CN 102216876 A 10/2011
JP 06-132875 A 5/1994
(Continued)

OTHER PUBLICATIONS

Extended European Search Report of EP Patent Application No. 14840415.5, dated Mar. 21, 2017, 09 pages.
(Continued)

*Primary Examiner* — John F Mortell
(74) *Attorney, Agent, or Firm* — Chip Law Group

(57) ABSTRACT

A wristband-type information processing device includes: a band section configured to be worn on a wrist of a user; a sensor unit configured to detect a motion of the user; a vibration signal generating unit configured to generate a first vibration signal for vibrating another associated wristband-type information processing device according to the motion detected by the sensor unit; and a communication unit configured to transmit the first vibration signal generated by the vibration signal generating unit to the other wristband-type information processing device.

17 Claims, 24 Drawing Sheets

(51) Int. Cl.
*G06F 3/01* (2006.01)
*H04M 1/725* (2006.01)
*H04M 19/04* (2006.01)
*H04B 1/3827* (2015.01)
*A61B 5/11* (2006.01)
*A61B 5/16* (2006.01)
*A61B 5/00* (2006.01)
*A61B 5/0205* (2006.01)

(52) U.S. Cl.
CPC ............ *G06F 1/163* (2013.01); *G06F 1/1684* (2013.01); *G06F 3/014* (2013.01); *G06F 3/016* (2013.01); *G06F 3/017* (2013.01); *H04B 1/385* (2013.01); *H04M 1/7253* (2013.01); *H04M 1/72519* (2013.01); *H04M 19/04* (2013.01); *A61B 5/0004* (2013.01); *A61B 5/02055* (2013.01); *A61B 2560/0242* (2013.01); *G06F 2200/1636* (2013.01); *G06F 2200/1637* (2013.01); *G06F 2203/011* (2013.01); *G06F 2203/0383* (2013.01); *H04B 2001/3861* (2013.01); *H04M 2250/12* (2013.01)

(56) References Cited

U.S. PATENT DOCUMENTS

| | | |
|---|---|---|
| 2005/0062841 A1 | 3/2005 | Rivera-Cintron |
| 2007/0139167 A1 | 6/2007 | Gilson et al. |
| 2008/0167006 A1 | 7/2008 | Hsi |
| 2010/0045619 A1 | 2/2010 | Birnbaum et al. |
| 2010/0123588 A1 | 5/2010 | Cruz Hernandez |
| 2010/0210323 A1* | 8/2010 | Collins ............. H04M 1/72547 455/575.1 |
| 2010/0238005 A1 | 9/2010 | White |
| 2011/0134026 A1 | 6/2011 | Kang et al. |
| 2011/0159921 A1* | 6/2011 | Davis ................ H04M 1/72569 455/556.1 |
| 2014/0111415 A1* | 4/2014 | Gargi ...................... G06F 3/017 345/156 |

FOREIGN PATENT DOCUMENTS

| | | |
|---|---|---|
| JP | HEI 06-132875 | 5/1994 |
| JP | 09-248315 A | 9/1997 |
| JP | 2000-194462 A | 7/2000 |
| JP | 2000-312696 | 11/2000 |
| JP | 2000-312696 A | 11/2000 |
| JP | 2001-148725 A | 5/2001 |
| JP | 2002-261901 | 9/2002 |
| JP | 2002-261901 A | 9/2002 |
| JP | 2005-328270 | 11/2005 |
| JP | 2005-328270 A | 11/2005 |
| JP | 2008-023127 A | 2/2008 |
| JP | 2009-188903 | 8/2009 |
| JP | 2009-188903 A | 8/2009 |
| JP | 2009-239773 A | 10/2009 |
| JP | 2011-115936 | 6/2011 |
| JP | 2011-115936 A | 6/2011 |
| JP | 2012-029066 | 2/2012 |
| JP | 2012-029066 A | 2/2012 |
| JP | 2012-048320 | 3/2012 |
| JP | 2012-048320 A | 3/2012 |
| JP | 2012-075089 A | 4/2012 |
| JP | 2012-216911 | 11/2012 |
| JP | 2012-216911 A | 11/2012 |
| WO | 2013/073437 | 5/2013 |
| WO | 2013/073437 A1 | 5/2013 |

OTHER PUBLICATIONS

Lopez-Meyer, et al.,"Detection of Hand-to-Mouth Gestures Using a RF Operated Proximity Sensor for Monitoring Cigarette Smoking",The Open Biomedical Engineering Journal, Jul. 2013, pp. 41-49.

Office Action for JP Patent Application No. 2015-534056, dated Jan. 23, 2018, 7 pages of Office Action and 4 pages of English Translation.

Office Action for CN Patent Application No. 201480046512.X, dated Apr. 4, 2018, 08 pages of Office Action and 10 pages of English Translation.

Final Office Action for U.S. Appl. No. 15/937,309, dated Mar. 5, 2019, 13 pages.

Office Action for JP Patent Application No. 2018-140268, dated Apr. 2, 2019, 04 pages of Office Action and 04 pages of English Translation.

\* cited by examiner

FIG. 22

| PATTERN ID | VIBRATION PATTERN | SOUND DATA | IMAGE DATA |
|---|---|---|---|
| PID_001 | Vib_012 | -- | -- |
| PID_002 | Vib_105 | Aud_023 | Img_041 |
| PID_003 | Vib_003 | -- | Img_005 |

FIG. 24

| PATTERN ID | VIBRATION PATTERN |
|---|---|
| PID_001 | Pat_Tap_001 |
| PID_002 | Pat_Tap_002 |
| PID_003 | Pat_Tap_003 |

WRISTBAND-TYPE INFORMATION PROCESSING DEVICE, INFORMATION PROCESSING SYSTEM, AND INFORMATION PROCESSING METHOD

TECHNICAL FIELD

The present disclosure relates to a wristband-type information processing device, an information processing system, an information processing method, and a program.

BACKGROUND ART

In recent years, as mobile terminals have spread, and network technology has become sophisticated, opportunities to perform communication via a network have increased. In this regard, techniques for implementing various communications using a network have been developed.

For example, an information processing device capable of performing communication by tactile stimulation without using language is disclosed in Patent Literature 1.

CITATION LIST

Patent Literature

Patent Literature 1: JP 2005-328270A

SUMMARY OF INVENTION

Technical Problem

However, in the technique disclosed in Patent Literature 1, for example, since a separate communication device for performing communication is necessary, it is difficult to perform communication casually.

In this regard, the present disclosure proposes a wristband-type information processing device, an information processing system, an information processing method, and a program, which are novel and improved and through which more casual and intimate communication can be implemented.

Solution to Problem

According to the present disclosure, there is provided a wristband-type information processing device including: a band section configured to be worn on a wrist of a user; a sensor unit configured to detect a motion of the user; a vibration signal generating unit configured to generate a first vibration signal for vibrating another associated wristband-type information processing device according to the motion detected by the sensor unit; and a communication unit configured to transmit the first vibration signal generated by the vibration signal generating unit to the other wristband-type information processing device.

According to the present disclosure, there is provided an information processing system including: a first wristband-type information processing device; and a second wristband-type information processing device associated with the first wristband-type information processing device. The first wristband-type information processing device includes a band section configured to be worn on a wrist of a first user, a sensor unit configured to detect a motion of the first user, a vibration signal generating unit configured to generate a first vibration signal for vibrating the associated second wristband-type information processing device, and a communication unit configured to transmit the first vibration signal generated by the vibration signal generating unit to the second wristband-type information processing device. The second wristband-type information processing device includes a band section configured to be worn on a wrist of a second user, a communication unit configured to receive the first vibration signal from the first wristband-type information processing device, and a vibrating unit configured to vibrate according to the first vibration signal received by the communication unit.

According to the present disclosure, there is provided an information processing method including: detecting a motion of a user; generating a first vibration signal for vibrating another associated wristband-type information processing device according to the detected motion; and transmitting the generated first vibration signal to the other wristband-type information processing device.

According to the present disclosure, there is provided a program causing a computer to function as: a sensor unit configured to detect a motion of a user; a vibration signal generating unit configured to generate a first vibration signal for vibrating another associated wristband-type information processing device according to the motion detected by the sensor unit; and a communication unit configured to transmit the first vibration signal generated by the vibration signal generating unit to the other wristband-type information processing device.

Advantageous Effects of Invention

As described above, according to the present disclosure, it is possible to implement more casual intimate communication. The above effect is not necessarily limited, and in addition to or instead of the above effect, any effect described in this specification or any other effect understood from this specification may be obtained.

BRIEF DESCRIPTION OF DRAWINGS

FIG. 22 is a diagram for describing output pattern selection by a wristband-type terminal according to the eighth embodiment.

FIG. 24 is a diagram for describing setting of a pattern ID in the wristband-type terminal according to the eighth embodiment.

DESCRIPTION OF EMBODIMENTS

Hereinafter, (a) preferred embodiment(s) of the present disclosure will be described in detail with reference to the appended drawings. In this specification and the drawings, elements that have substantially the same function and structure are denoted with the same reference signs, and repeated explanation is omitted.

The description will proceeds in the following order.
1. Overview of communication system according to embodiment of present disclosure
2. Embodiments
2-1. Basic configuration
2-1-1. External configuration
2-1-2. Internal configuration
2-2. Embodiments
2-2-1. First embodiment
2-2-2. Second embodiment
2-2-3. Third embodiment
2-2-4. Fourth embodiment
2-2-5. Fifth embodiment
2-2-6. Sixth embodiment
2-2-7. Seventh embodiment
2-2-8. Eighth embodiment
3. Conclusion 1. OVERVIEW OF COMMUNICATION SYSTEM ACCORDING TO EMBODIMENT OF PRESENT DISCLOSURE Commonly, a person at a remote site performs communication by a voice call or a video call using a mobile terminal such as a mobile phone or a smartphone. However, such communication has a problem in that there are cases in which it is difficult to perform communication casually. For example, in order to make a phone call using a mobile terminal, a motion of inputting a telephone number and making a call and a motion of putting a speaker to one's ear and putting a microphone to one's lips are necessary, and there are cases in which a call is not answered and not connected. Further, when there is no topic to begin with, it is hard to make a phone call. In addition, a person who receives a phone call has to take a mobile terminal out of his/her pocket, bag, or the like, stop what he/she is doing, and move to a quiet place where a phone call is possible.

In the technique disclosed in Patent Literature 1, for example, since a device that inputs and outputs tactile stimulation has to be held in a hand, or a communication device for performing communication is separately necessary, it is difficult to communicate casually. Further, in the technique disclosed in Patent Literature 1, communication problems of the mobile terminal are not solved at all.

In this regard, a communication system according to an embodiment of the present disclosure was invented in light of the foregoing. More casual intimate communication can be implemented through the communication system according to an embodiment of the present disclosure. More specifically, the communication system according to an embodiment of the present disclosure enables communication of exchanging greetings to be performed with a specific person frequently without reluctance. An overview of the communication system according to an embodiment of the present disclosure will be described below with reference to FIG. 1.

Figure 1:
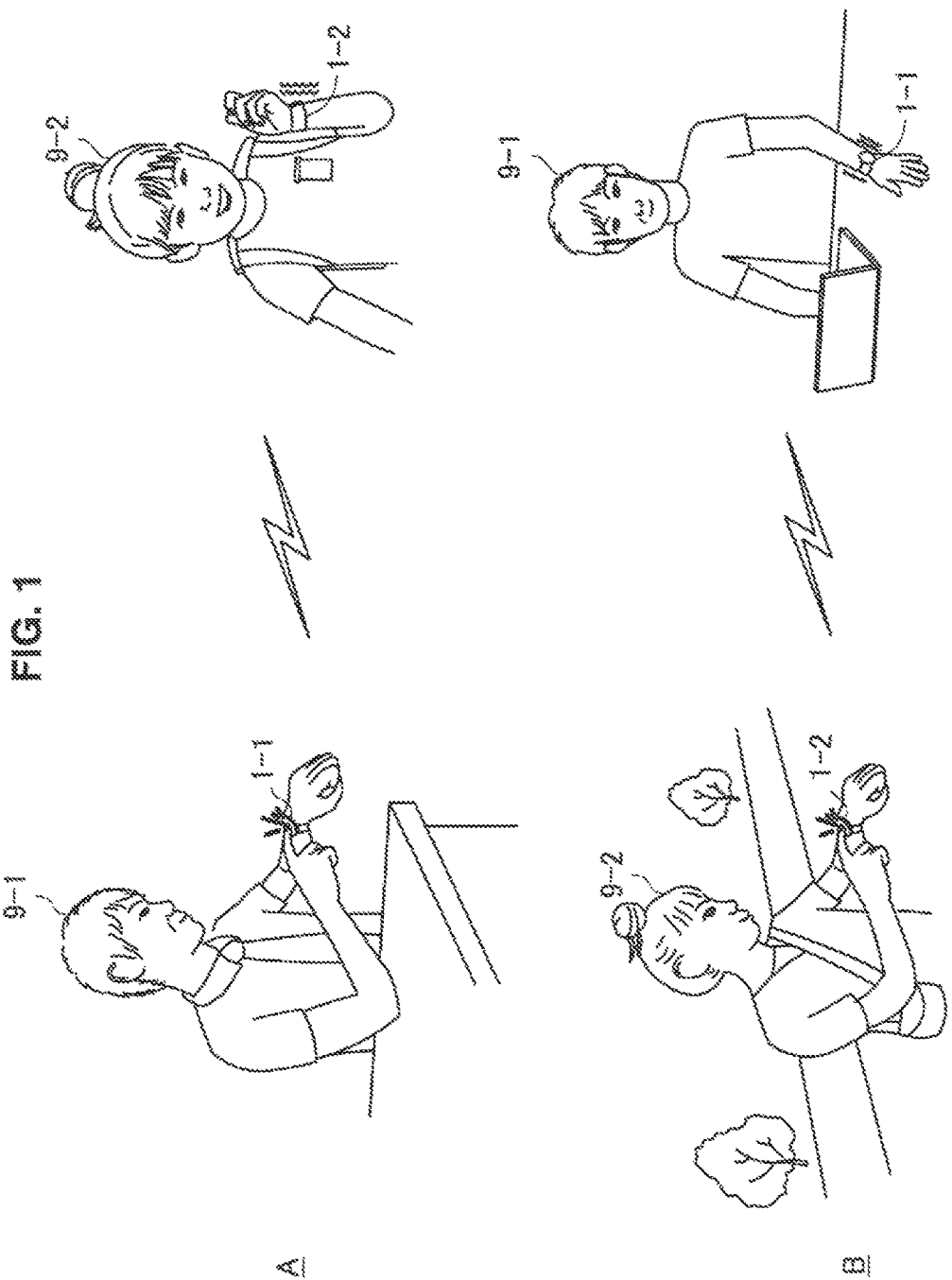
FIGS. 1A and 1B are explanatory diagrams illustrating an overview of a communication system according to an embodiment of the present disclosure.

FIG. 1 is an explanatory diagram illustrating an overview of the communication system according to an embodiment of the present disclosure. As illustrated in FIG. 1, a user 9-1 wears a wristband-type terminal (a first wristband-type information processing device) 1-1 on his wrist, and a user 9-2 wears a wristband-type terminal 1-2 (a second wristband-type information processing device) on her wrist. Here, the user 9-1 is a father, and the user 9-2 is his daughter. When the wristband-type terminal 1-1 and the wristband-type terminal 1-2 need not be particularly distinguished from each other, they are referred to collectively as a "wristband-type terminal 1."

For example, a situation in which the father (the user 9-1) gives the daughter (the user 9-2) a morning greeting while living apart from his family is assumed. In this case, as illustrated in FIG. 1A, the user 9-1 taps the wristband-type terminal 1-1. Hereinafter, such an input motion is also referred to as a "tapping input" The tapping input refers to an input method of causing vibration, pressure, contact, or the like to occur in a device according to the user's motion such as pressing or stroking in addition to a tapping motion. The wristband-type terminal 1-1 is associated with the wristband-type terminal 1-2 in advance, and transmits information indicating that it is tapped to the wristband-type terminal 1-2 so that the wristband-type terminal 1-2 vibrates. Thus, the user 9-2 can feel a touch as if her wrist is tapped by the user 9-1 and have a feeling of receiving a morning greeting from the user 9-1. Hereinafter, such vibration is also referred to as "tapping vibration."

Here, the user 9-1 can communicate with the user 9-2 by simply tapping the wristband-type terminal 1-1 instead of performing a motion of inputting a telephone number and making a call and a motion of putting a speaker to his ear and putting a microphone to his lips. Since the wristband-type terminal 1-2 worn on the wrist simply vibrates, the user 9-2 need not take a mobile terminal out of her pocket, bag, or the like, stop what she is doing, or move to a quiet place. Further, since the wristband-type terminals 1-1 and 1-2 are worn on the wrists and can perform communication by themselves, it is unnecessary to hold the device that inputs and outputs tactile stimulation in his/her hand or carry the separate communication device for performing communication. Moreover, communication is possible even without a topic. As described above, casual communication can be implemented through the communication system according to the present embodiment.

Further, a scenario in which the daughter (the user 9-2) is on vacation or outside after school and worries about the health of her father (the user 9-1) who is working on a day off or working overtime is assumed. In this case, as illustrated in FIG. 1B, the user 9-2 taps the wristband-type terminal 1-2. The wristband-type terminal 1-2 is associated with the wristband-type terminal 1-1 in advance, and transmits information indicating that it is tapped to the wristband-type terminal 1-1. Thus, since the wristband-type terminal 1-1 vibrates, the user 9-1 can feel a touch as if his wrist were being tapped by the user 9-2 and feel that the user 9-2 is worrying about his health. Of course, the user 9-1 may inform the user 9-2 that he is healthy as a response by tapping the wristband-type terminal 1-1.

As described above, the communication system according to the present embodiment can implement communication of transmitting the tapping vibration even when the users are away from each other. Here, family members, couples, and close friends express intimacy by touching each other every day. In the communication system according to the present embodiment, similarly to when they actually touch each other, one user taps, and the other user feels a touch as if he/she were being tapped, and thus both the tapping user and the tapped user can feel intimate communication. Further, the user 9 can communicate with the other party simply by tapping the wristband-type terminal 1 and thus have a feeling of staying connected with an important person constantly. Communication of transmitting the tapping vibration through the communication system according to the present embodiment is also referred to as "tapping communication."

The communication system according to the present embodiment can be applied to various scenarios in addition to the scenario described with reference to FIGS. 1A and 1B. For example, when a brother or sister is away from his/her family on a trip or an overnight stay, an emotion such as "good luck" or "it's okay" can be transmitted. Further, intimate communication can be casually performed between grandparents and grandchildren or between cousins who live in separate places. Furthermore, daily signals such as "come home now" or "it is time to eat" can be casually given between a parent and a child. Moreover, the communication system may be used between a couple or may be used between one person and many persons.

The overview of the communication system according to an embodiment of the present disclosure has been described above. Next, exemplary embodiments will be described in detail with reference to FIGS. 2 to 24.

2. EMBODIMENTS

2-1. Basic Configuration

2-1-1. External Configuration

First, an exemplary external configuration of the wristband-type terminal 1 that is common to the embodiments of the present disclosure will be described with reference to FIG. 2 and FIG. 3.

Figure 2:
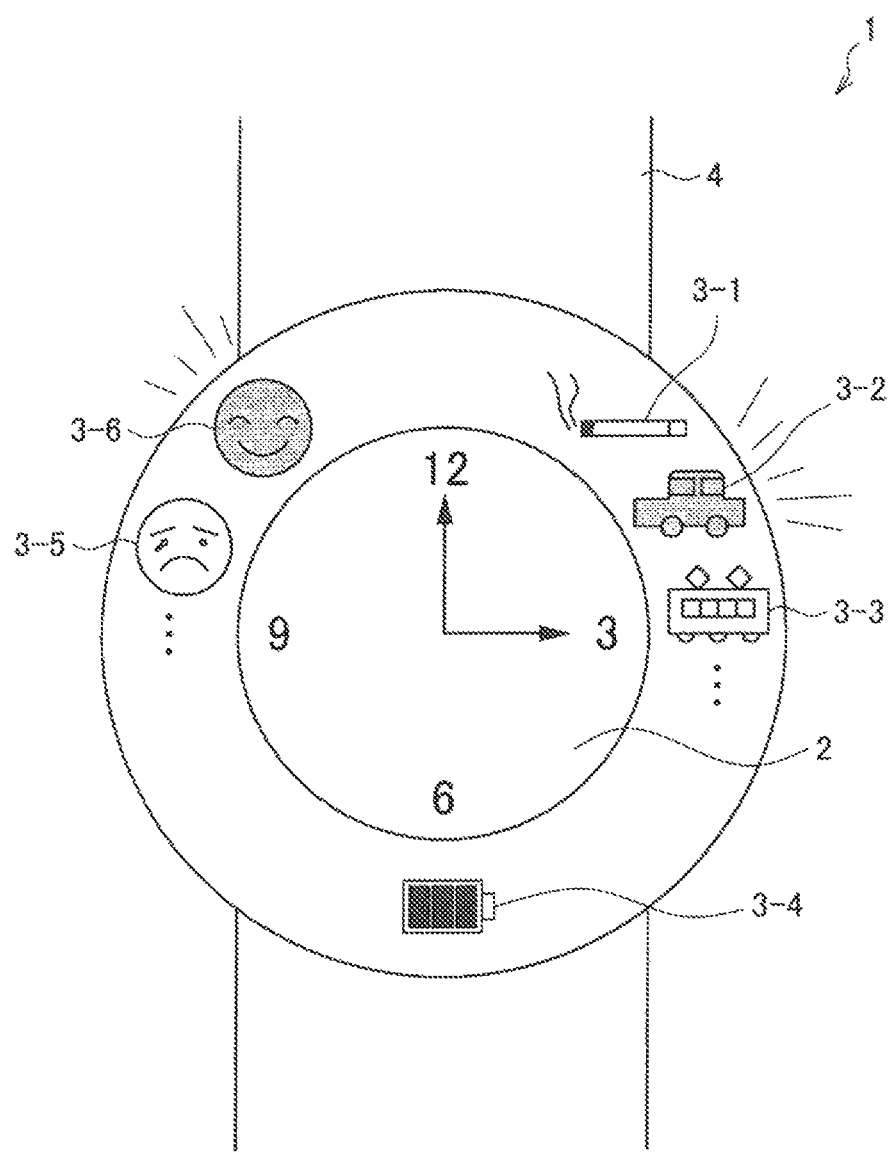
FIG. 2 is a diagram illustrating an exemplary external configuration of a wristband-type terminal according to an embodiment of the present disclosure.

FIG. 2 is a diagram illustrating an exemplary external configuration of wristband-type terminal 1 according to an embodiment of the present disclosure. As illustrated in FIG. 2, the wristband-type terminal 1 according to the present embodiment includes a clock 2, LEDs 3-1 to 3-6, and a band section 4 as an example. When the LEDs 3-1 to 3-6 need not be particularly distinguished from one another, they are referred to collectively as an "LED 3."

For example, the band section 4 is formed similarly to bands for wristwatches made of leather, a metal, a fiber, or rubber. The wristband-type terminal 1 is worn on the wrist of the user using the band section 4.

The clock 2 has a function of displaying a current time. The wristband-type terminal 1 further includes a vibration sensor and a pressure sensor, and the user can transmit the tapping vibration to another user (hereinafter, also referred to simply as the "other party") wearing another wristband-type terminal 1 associated therewith by tapping an area of the clock 2. The wristband-type terminal 1 is assumed to be used by a young child who has neither a mobile phone nor a smartphone. The analog clock 2 illustrated in FIG. 2 is effective for intellectual education of children. Further, when the wristband-type terminal 1 has a Global Positioning System (OPS) function, it is also effective for safety confirmation of children. Meanwhile, parents may use a device that simply has a function of transmitting the tapping vibration to children such as the vibration sensor or the pressure sensor but does not include the clock 2 or the like.

The LED 3 has a function of notifying the user of information indicating a state such as behavior, a feeling, or a surrounding environment of the other party. For example, the wristband-type terminal 1 gives the user a notification indicating that the other party is smoking through the LED 3-1, a notification indicating that the other party is in a car through the LED 3-2, and a notification indicating that the other party is on a train through the LED 3-3. Further, the wristband-type terminal 1 gives the user a notification indicating that the other party is sad through the LED 3-5 and a notification indicating that the other party is happy through the LED 3-6. For example, in the example illustrated in FIG. 2, since the LED 3-2 and the LED 3-6 are turned on, the user understand that the other party is in a car and happy. As described above, since the user can know the state of the other party through the LED 3, the user can transmit the tapping vibration indicating an emotion such as "a greeting," "encouragement," or "a reminder not to smoke too much" to the other party according to the state of the other party.

The LED 3 further has a function of notifying the user of a state of the wristband-type terminal 1. For example, the wristband-type terminal 1 notifies the user of a remaining battery level through the LED 3-4.

The exemplary external configuration of the wristband-type terminal 1 has been described above. Next, another exemplary external configuration of the wristband-type terminal 1 will be described with reference to FIG. 3.

Figure 3:
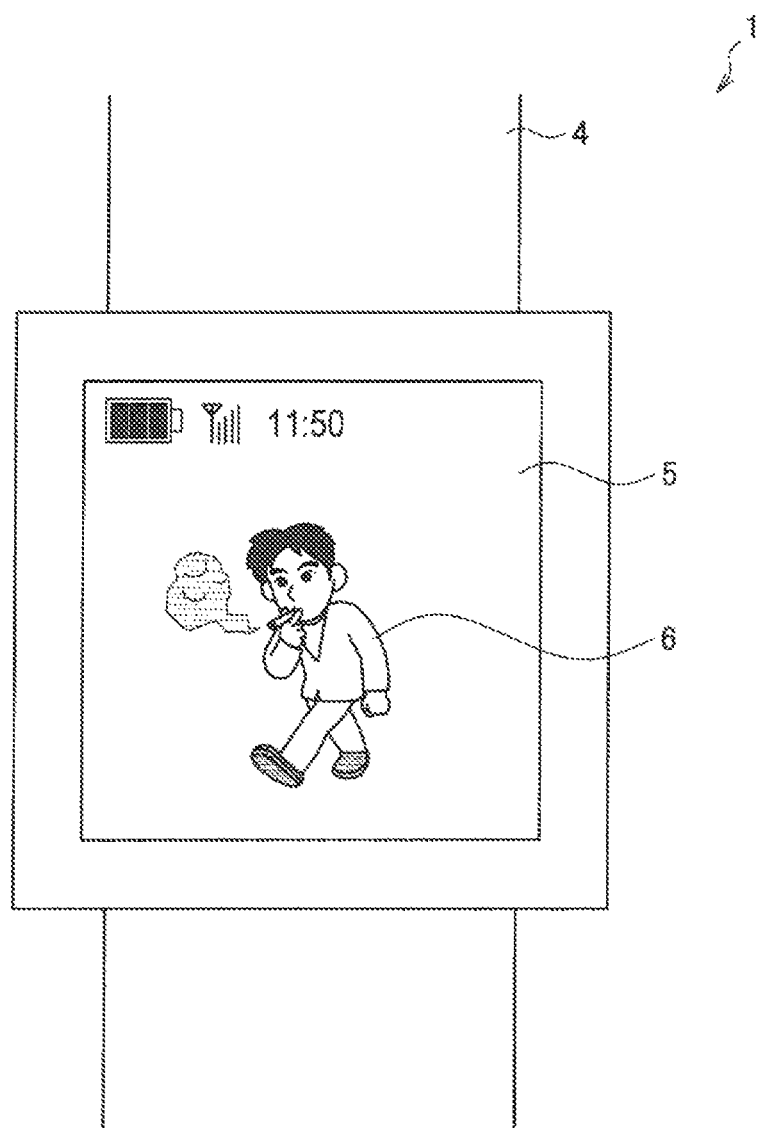
FIG. 3 is a diagram illustrating an exemplary external configuration of a wristband-type terminal according to an embodiment of the present disclosure.

FIG. 3 is a diagram illustrating an exemplary external configuration of the wristband-type terminal 1 according to an embodiment of the present disclosure. As illustrated in FIG. 3, the wristband-type terminal 1 according to the present embodiment includes a band section 4 and a display section 5 as an example.

The display section 5 has a function of notifying the user of information indicating the state of the other party such as behavior, a feeling, or a surrounding environment, similarly to the LED 3. For example, the display section 5 notifies the user of the information, for example, through a facial expression or a motion of an avatar 6. In the example illustrated in FIG. 3, the other party gives the user a notification indicating he/she is smoking. The user can transmit the tapping vibration to the other party by tapping the area of the display section 5.

The wristband-type terminal 1 may be associated with a plurality of other parties. For example, the wristband-type terminal 1 may notify the user of states of a plurality of other parties by displaying a plurality of avatars 6 on the display section 5. Further, the wristband-type terminal 1 may display the state of the user wearing the wristband-type terminal 1 through the avatar 6 indicating the user.

Further, as illustrated in FIG. 3, the display section 5 may notify the user of information indicating a remaining battery level, radio field strength, or a time.

The exemplary external configuration of the wristband-type terminal 1 has been described above. Next, an internal configuration of the wristband-type terminal 1 that is common to the embodiments of the present disclosure will be described with reference to FIG. 4.

2-1-2. Internal Configuration

Figure 4:
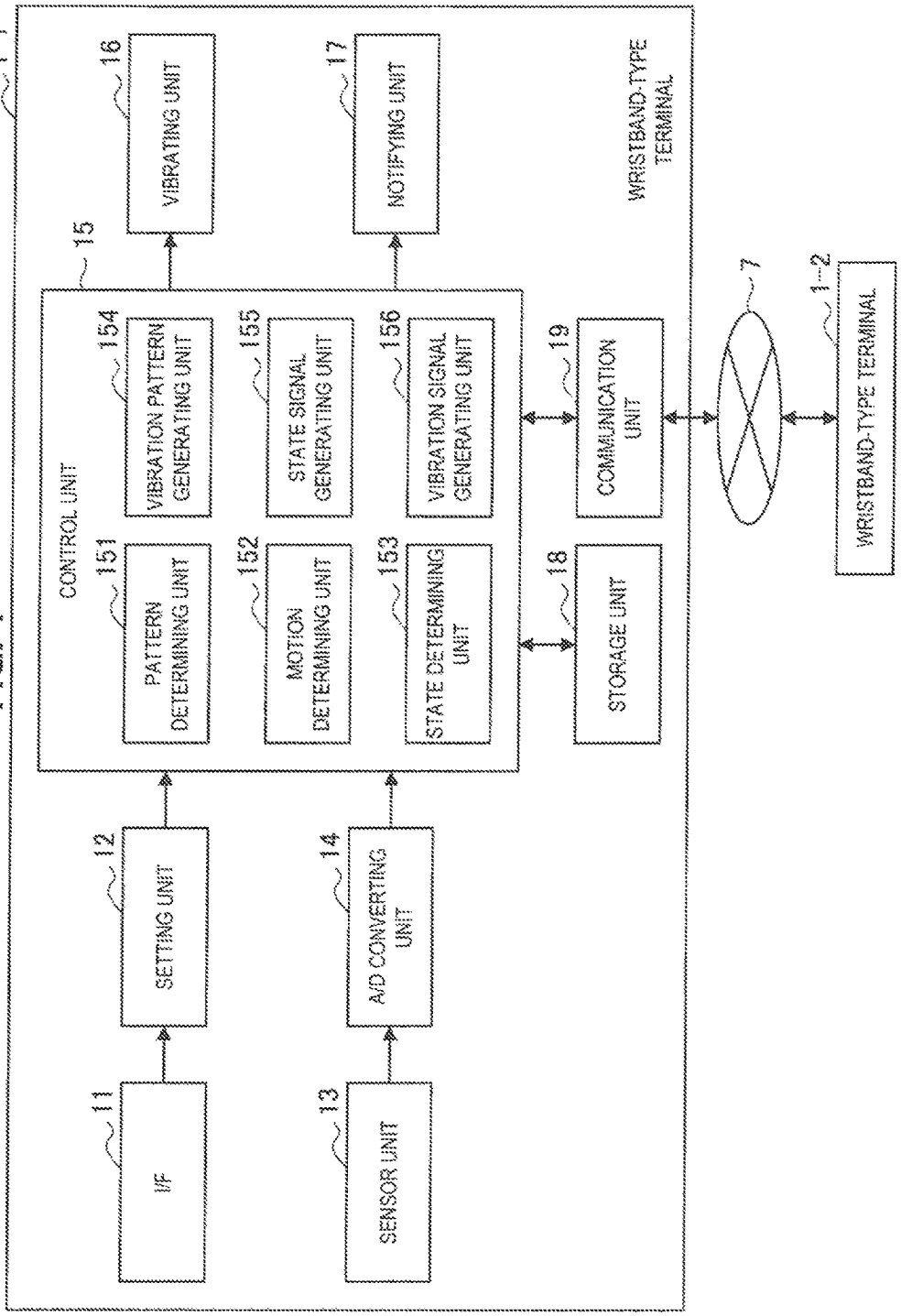
FIG. 4 is an explanatory diagram illustrating an internal configuration of a wristband-type terminal according to an embodiment of the present disclosure.

FIG. 4 is an explanatory diagram illustrating an internal configuration of the wristband-type terminal 1 according to an embodiment of the present disclosure. As illustrated in FIG. 4, a wristband-type terminal 1-1 includes an I/F 11, a setting unit 12, a sensor unit 13, an A/D converting unit 14, a control unit 15, a vibrating unit 16, a notifying unit 17, a storage unit 18, and a communication unit 19. The wristband-type terminal 1-1 (the wristband-type information processing device) is associated with a wristband-type terminal 1-2 (another wristband-type information processing device) and tapping communicates with the wristband-type terminal 1-2. A person wearing the wristband-type terminal 1-1 is also referred to as the user, and a person wearing the wristband-type terminal 1-2 is also referred to as the other party. The wristband-type terminal 1-2 has the same internal configuration as the wristband-type terminal 1-1.

(I/F 11)

The I/F 11 is a connecting device for connecting the wristband-type terminal 1 with another information processing device. The I/F 11 is implemented, for example, by a Universal Serial Bus (USB) connector or the like and connected to a Personal Computer (PC) or a notebook PC.

(Setting Unit 12)

The setting unit 12 has a function of setting the other party with which the wristband-type terminal 1-1 performs the tapping communication. Specifically, the setting unit 12 has a function of performing a setting of associating with another wristband-type terminal 1 different from the wristband-type terminal 1-2 according to a user input performed through the I/F 11. For example, the setting unit 12 sets a telephone number of the other party. Thus, the user can perform the tapping communication while switching a plurality of other parties.

(Sensor Unit 13)

The sensor unit 13 has a function of acquiring the state such as a motion or a feeling of the user. For example, the sensor unit 13 is implemented by a camera, a microphone, a GPS, an infrared sensor, an illuminance sensor, a vibration sensor, a pressure sensor, a thermometer, a hygrometer, a barometer, a clock, a gyro sensor, an acceleration sensor, a touch sensor, or the like. The sensor unit 13 may include a sensor that detects biometric information of the user such as a galvanic skin response (GSR) sensor that detects sweating, a myoelectric sensor that detects myoelectricity, a neural sensor that detects an electric signal of a nerve, a pulsimeter, or a clinical thermometer. The sensor unit 13 detects a tapping input (a motion of the user) of the user to the wristband-type terminal 1 through the vibration sensor, the pressure sensor, the touch sensor, or the like. In addition, the sensor unit 13 detects whether or not the user is wearing the wristband-type terminal 1-1 through the touch sensor, the illuminance sensor, the clinical thermometer, or the pulsimeter installed in the band section 4. The sensor unit 13 outputs information indicating a sensing result to the A/D converting unit 14.

(A/D Converting Unit 14)

The A/D converting unit 14 is an electric circuit that converts an analog electric signal into a digital electric signal. The AD converting unit 14 converts an analog signal indicating the sensing result output from the sensor unit 13 into a digital signal, and outputs the digital signal.

(Control Unit 15)

The control unit 15 functions as an operation processing device and a control device, and controls an operation of the wristband-type terminal 1-1 in general according to various kinds of programs. The control unit 15 is implemented, for example, by a Central Processing Unit (CPU) or a microprocessor. The control unit 15 may include a Read Only Memory (ROM) that stores a program to be used, an operation parameter, or the like and a Random Access Memory (RAM) that temporarily stores an appropriately changing parameter or the like.

As illustrated in FIG. 4, the control unit 15 functions as a pattern determining unit 151, a motion determining unit 152, a state determining unit 153, a vibration pattern generating unit 154, a state signal generating unit 155, and a vibration signal generating unit 156.

Motion Determining Unit 152

The motion determining unit 152 has a function of determining whether or not a motion detected by the sensor unit 13 is a predetermined motion. More specifically, the motion determining unit 152 determines whether or not a motion of the user is a tapping input based on vibration detected by the sensor unit 13. For example, the motion determining unit 152 stores a pattern of strength or a period of vibration, and determines whether or not the motion of the user is the tapping input, for example, based on whether or not an amplitude of a vibration waveform obtained by the sensor unit 13 exceeds a threshold value or whether or not a pattern of a period is identical to a stored pattern. The motion determining unit 152 can distinguish vibration performed by a motion unintended by the user from an intended tapping input and thus prevent a malfunction.

Vibration Signal Generating Unit 156

The vibration signal generating unit 156 has a function of generating a vibration signal (a first vibration signal) for vibrating the associated wristband-type terminal 1-2 according to the tapping input detected by the sensor unit 13. More specifically, the vibration signal generating unit 156 generates the vibration signal when the motion determining unit 152 determines the motion of the user to be the tapping input. The vibration signal generated by the vibration signal generating unit 156 is transmitted to the wristband-type terminal 1-2, and thus the tapping vibration is transmitted to the other party.

The vibration signal may be a vibration waveform indicating the vibration that the wristband-type terminal 1-1 has received through the tapping input or information (flag) simply indicating that the tapping motion has been detected. When the vibration signal is the vibration waveform, the wristband-type terminal 1-2 vibrates based on the vibration waveform, and thus a tap rhythm or strength of the user is transmitted faithfully to the other party. When the vibration signal is the information (flag) simply indicating that the tapping motion has been detected, a tapping vibration according to a previously set vibration pattern is transmitted to the other party. In this case, since information to be transmitted is small, the tapping vibration is rapidly transmitted to the other party.

State Determining Unit 153

The state determining unit 153 has a function of determining whether or not the state detected by the sensor unit 13 is a predetermined state. More specifically, the state determining unit 153 determines whether or not the detected state is a state such as "standing still," "sitting," "walking," "running," "jumping," "riding a bicycle," "riding a train," "riding a bus," "standing and operating the wristband-type terminal 1," "sitting and operating the wristband-type terminal 1," or "not wearing the wristband-type terminal 1" based on vibration, an inclination, a sound, a pulse, or the like acquired by the sensor unit 13.

In addition, the state determining unit 153 determines whether or not the detected state corresponds to a state such as "riding an elevator" and "riding an escalator" based on atmospheric pressure acquired by the sensor unit 13. The state determining unit 153 determines whether or not the detected state corresponds to a feeling such as "happy," "sad," "excited," or "anxious" or a physical condition such as "relaxed" or "sick with a cold" based on a body temperature or a pulse acquired by the sensor unit 13. The state determining unit 153 determines whether or not the detected state corresponds to a state such as "at home" or "at work" based on position information acquired by the sensor unit 13. The state determining unit 153 determines whether or not the detected state corresponds to a state such as "sleeping" or "eating breakfast" based on time information acquired by the sensor unit 13. The state determining unit 153 determines whether or not the detected state corresponds to a state such as "in a hot place," or "in a cold place," or "outside" based on an air temperature or humidity acquired by the sensor unit 13.

Further, when the wristband-type terminal 1 is worn on a dominant hand of the user, the state determining unit 153 determines whether or not the detected state corresponds to a state such as "writing" or "typing on a keyboard" based on acceleration of the dominant hand. Furthermore, the state determining unit 153 may determine a stroke order and specifically specify text being written by the user. Moreover, the state determining unit 153 determines whether or not the detected state corresponds to a state such as "smoking" or "drinking" based on a motion in which the dominant hand moves back and forth between his/her lips and a table or the like.

State Signal Generating Unit 155

The state signal generating unit 155 has a function of generating a state signal (a first state signal) for notifying the other party wearing the wristband-type terminal 1-2 of the state of the user detected by the sensor unit 13. More specifically, the state signal generating unit 155 generates the state signal indicating the state determined by the state determining unit 153. The state signal generated by the state signal generating unit 155 is transmitted to the wristband-type terminal 1-2, so that a notification indicating the state of the user such as "walking" or "smoking" is given to the other party. Thus, the user can perform communication of informing the other party of his/her state without taking an active motion such as a particular motion of making a phone call.

Vibration Pattern Generating Unit 154

The vibration pattern generating unit 154 has a function of generating vibration pattern information (first vibration pattern information) indicating a vibration pattern of the tapping input by the user which is detected by the sensor unit 13. Here, the vibration pattern information is information including a pattern of strength or a period of vibration such as information indicating a rhythm of the tapping input. The vibration pattern information generated by the vibration pattern generating unit 154 is transmitted to the wristband-type terminal 1-2 through the communication unit 19.

Pattern Determining Unit 151

The pattern determining unit 151 has a function of comparing two pieces of vibration pattern information and determining whether or not the two pieces of vibration pattern information are identical to each other. The pattern determining unit 151 performs three pattern determinations described below.

Firstly, the pattern determining unit 151 functions as a first pattern determining unit that determines whether or not the user of the wristband-type terminal 1-1 and the user of the wristband-type terminal 1-2 have performed the tapping input at the same timing. Specifically, the pattern determining unit 151 determines whether or not the vibration pattern information (first vibration pattern information) generated by the vibration pattern generating unit 154 is identical to the vibration pattern information (second vibration pattern information) generated by the wristband-type terminal 1-2. For example, when timings at which the amplitudes of the vibration patterns indicated by the respective vibration pattern information have exceeded a predetermined threshold value, that is, timings at which the users have tapped the wristband-type terminal 1 with their fingers are the same timings or within a predetermined error range, the pattern determining unit 151 determines that the two pieces of vibration pattern information are identical to each other. A notification indicating the determination result obtained by the pattern determining unit 151 is given to the user through the notifying unit 17 which will be described later, and thus the user can understand whether or not he/she has performed the tapping input at the same timing as the other party.

Secondly, the pattern determining unit 151 functions as a second pattern determining unit that determines a tapping communication end timing. Specifically, the pattern determining unit 151 determines whether or not a vibration pattern indicated by the vibration pattern information (the first vibration pattern information) generated by the vibration pattern generating unit 154 is identical to a predetermined vibration pattern (a third vibration pattern) indicating an end condition. For example, when a timing at which the amplitude indicated by the vibration pattern information has exceed a predetermined threshold value, that is, a rhythm in which the user has tapped the wristband-type terminal 1 with his/her finger is a predetermined rhythm, the pattern determining unit 151 determines that the vibration pattern indicated by the vibration pattern information is identical to the predetermined vibration pattern indicating the end condition. The determination result obtained by the pattern determining unit 151 is transmitted to the wristband-type terminal 1-2 through the communication unit 19 which will be described later, so that the user of the wristband-type terminal 1-2 is notified of the determination result. Thus, the user of the wristband-type terminal 1-2 can understand that the user of the wristband-type terminal 1-1 desires to end the tapping communication, that is, the tapping communication end timing.

Thirdly, the pattern determining unit 151 functions as a third pattern determining unit that determines whether or not a previously set output such as a sound output or a screen display is performed in the wristband-type terminal 1-2. Specifically, the pattern determining unit 151 determines whether or not the vibration pattern indicated by the vibration pattern information (the first vibration pattern information) generated by the vibration pattern generating unit 154 is identical to a predetermined vibration pattern (a fourth vibration pattern). For example, when a timing at which the amplitude indicated by the vibration pattern information has exceeded a predetermined threshold value, that is, a rhythm in which the user has tapped the wristband-type terminal 1 with his/her finger is a predetermined rhythm, the pattern determining unit 151 determines that the vibration pattern indicated by the vibration pattern information is identical to the predetermined vibration pattern. The determination result obtained by the pattern determining unit 151 is transmitted to the wristband-type terminal 1-2 through the communication unit 19 which will be described later, and then an output such as a sound output or an image display according to the determination result obtained by the wristband-type terminal 1-2 is performed. The wristband-type terminal 1-2 may vibrate according to the determination result.

(Vibrating Unit 16)

The vibrating unit 16 vibrates the wristband-type terminal 1-1 according to control by the control unit 15. More specifically, when the vibration signal (the second vibration signal) generated according to the tapping input of the other party is received from the wristband-type terminal 1-2 through the communication unit 19, the vibrating unit 16 vibrates according to the vibration signal. The vibrating unit 16 may vibrate according to a predetermined vibration pattern that is decided in advance or may reproduce the tapping motion of the other party by vibrating based on the vibration waveform when the received vibration signal is a vibration waveform.

The vibrating unit 16 may vibrate according to the state signal received from the wristband-type terminal 1-2. For example, the wristband-type terminal 1-1 is assumed to receive a state signal indicating that the other party is "running" from the wristband-type terminal 1-2. In this case, the vibrating unit 16 may vibrate in synchronization with a heart rate of the other party detected by the pulsimeter installed in the sensor unit 13 of the wristband-type terminal 1-2. Further, the notifying unit 17 may output a sound "panting" as when a dog runs according to the heart rate of the other party through a speaker, a headphone, or the like. Through such output, the user can feel, for example, the state in which the other party is running with a sense of realism.

(Notifying Unit 17)

When a state signal (the second state signal) generated according to the state of the other party is received from the wristband-type terminal 1-2 through the communication unit 19, the notifying unit 17 notifies the user of information indicating the state of the other party according to the received state signal. Specifically, the notifying unit 17 notifies the user of information on the state such as a feeling or behavior of the other party such as "happy" or "smoking." The notifying unit 17 is implemented, for example, by the LED 3 described above with reference to FIG. 2, the display section 5 described above with reference to FIG. 3, a speaker that outputs a sound, or the like. Similarly, the wristband-type terminal 1-2 also includes the notifying unit 17, and a notification of information indicating the state such as a feeling or behavior of the user of the wristband-type terminal 1-1 is given to the other party through the notifying unit 17 of the wristband-type terminal 1-2.

The communication of giving a notification indicating one's state to the other party and receiving a notification indicating the state of the other party functions as a trigger of encouraging the tapping input. For example, when the user is notified that the other party is smoking, the user transmits an emotion such as "be careful not to smoke too much" to the other party through the tapping vibration using the notification as a trigger. In addition, the notifying unit 17 can provide the trigger for the tapping input to the user by notifying of a change in a feeling such as excited or anxious, a change in a physical condition such as tired or drinking, or a change in an environment such as hot/muggy/cold. Further, the notifying unit 17 may be configured to be capable of simply notifying of walking, use of a bus or a train, or staying outside, and may encourage the tapping input more strongly by displaying a mark indicating that such behavior has continued for a long time on the avatar 6 or turning on the LED 3.

Further, the notifying unit 17 notifies the user of what is used as the trigger by which the tapping vibration is transmitted from the other party. More specifically, when the vibration signal (the second vibration signal) generated according to the tapping input of the other party is received from the wristband-type terminal 1-2 after the state signal (the first state signal) indicating the state of the user is transmitted through the communication unit 19, the notifying unit 17 notifies the user of the state of the user serving as the trigger for the tapping input. For example, when the other party notices that the user is smoking through lighting of the LED 3 or display of the avatar 6 and then performs the tapping input, the notifying unit 17 gives a notification indicating that the other party has transmitted the tapping vibration with respect to smoking of the user to the user. Thus, the user can understand that the other party is worrying about his/her smoking, so that more intimate communication is implemented.

Further, the wristband-type terminal 1-1 is assumed to receive information indicating the state of the user serving as the trigger for the tapping input from the wristband-type terminal 1-2 and notify the user of the state of the user serving as the trigger based on the information. In addition, the wristband-type terminal 1-1 may store the state signal when transmitting the state signal and notify the user of the state of the user based on the stored state signal when the vibration signal is received.

Further, when the vibration signal (the second vibration signal) is received from the wristband-type terminal 1-2 through the communication unit 19, the notifying unit 17 notifies the user of information indicating an incoming call type based on a result of determining whether or not the user is wearing the wristband-type terminal 1-1 through the sensor unit 13. More specifically, when the user is detected not to be wearing the wristband-type terminal 1-1, the notifying unit 17 gives a notification indicating that there is a missed incoming call to the user, whereas when the user is detected to be wearing the wristband-type terminal 1-1, the notifying unit 17 gives a notification indicating that there is an incoming call to the user. The notifying unit 17 notifies the user of information indicating that the vibration signal has been received from the wristband-type terminal 1-2 as the notification indicating that there is a missed incoming call, and notifies the user of information indicating that vibration has been performed based on the vibration signal received from the wristband-type terminal 1-2 as the notification indicating that there is an incoming call. For example, the notifying unit 17 notifies the user of a missed incoming call or an incoming call by displaying a mark indicating the incoming call type or the avatar 6 indicating the other party serving as a transmission source of the vibration signal or turning on the LED 3. As a result, even when the user is not wearing the wristband-type terminal 1-1 but the tapping communication is performed, the user can understand that there was the tapping communication for the user, that is, that the other party has attempted communication. Further, since a missed incoming call serves as a trigger for encouraging the tapping input, communication is further promoted. Further, when the user is detected to be sleeping through the illuminance sensor, the pulsimeter, or the like installed in the sensor unit 13, the notifying unit 17 may notify of a missed incoming call without performing the tapping vibration. Thus, the wristband-type terminal 1-1 can prevent the user's sleep from being disturbed. Hereinafter, a notification indicating that there is a missed incoming call is also referred to as a "missed incoming call notification," and a notification indicating that there is an incoming call is also referred to as an "incoming call notification."

Further, when the vibration signal (the first vibration signal) is transmitted to the wristband-type terminal 1-2 through the communication unit 19, the notifying unit 17 notifies the user of information indicating whether or not the other party is wearing the wristband-type terminal 1-2. In other words, the notifying unit 17 notifies the user of information indicating whether or not the tapping vibration transmitted from the user to the other party has been transmitted to the other party. For example, the notifying unit 17 notifies the user of the information indicating the incoming call type in the wristband-type terminal 1-2. Thus, the user can understand whether or not the tapping vibration has been transmitted to the other party, and thus even when there is no response of the tapping vibration from the other party, the user does not worry unnecessarily.

Further, the notifying unit 17 notifies the user of the determination result obtained by the pattern determining unit 151. For example, the notifying unit 17 gives a notification indicating whether or not the tapping input has been performed at the same timing as the other party or gives a notification indicating the tapping communication end timing.

(Storage Unit 18)

The storage unit 18 is a part that records and reproduces data in a predetermined recording medium. The storage unit 18 is implemented, for example, as a Hard Disc Drive (HDD). Of course, various media such as a solid state memory such as a flash memory, a memory card built in a solid state memory, an optical disc, a magneto-optical disc, and a holographic memory are considered as the recording medium, and it is preferable to employ a configuration capable of performing recording and reproduction on a recording medium employed as the storage unit 18.

The wristband-type terminal 1 according to the present embodiment can set the user as the other party of the tapping communication. For example, the user stores biometric information such as a pulse, breathing, or a body temperature when he/she is irritated in the wristband-type terminal 1. The wristband-type terminal 1 determines that the user is irritated next time based on the biometric information and performs the tapping vibration, and thus can help the user calm down and control his/her feeling of irritation.

In order to implement the tapping vibration for the user, the storage unit 18 stores the state of the user detected by the sensor unit 13. More specifically when a storage instruction is input to an operation unit (not illustrated) from the user or when the tapping input is performed, the storage unit 18 stores the biometric information indicating the state of the user detected by the sensor unit 13. At this time, the storage unit 18 may store information indicating the state of the user determined by the state determining unit 153. In this case, when a state that is the same as or similar to the state of the user stored in the storage unit 18 is detected by the sensor unit 13, the vibrating unit 16 vibrates.

Further, the storage unit 18 stores information for outputting a sound output, an image display, or the like according to the tapping input. More specifically, the storage unit 18 stores a pattern of the tapping input in association with a sound or an image output when the pattern is input.

(Communication Unit 19)

The communication unit 19 is a communication module for performing wired or wireless communication with the wristband-type terminal 1-2 associated through the setting unit 12 based on control by the control unit 15. For example, the communication unit 19 is connected to the Internet, 3G/Long Term Evolution (LTE), or the like, and performs communication with the wristband-type terminal 1-2 via a network 7 illustrated in FIG. 4. The communication unit 19 may perform communication directly with the wristband-type terminal 1-2 through Bluetooth (a registered trademark) or the like.

In the present embodiment, the communication unit 19 transmits the vibration signal (the first vibration signal) generated according to the tapping input of the user by the vibration signal generating unit 156 to the wristband-type terminal 1-2. Thus, the wristband-type terminal 1-2 vibrates according to the received vibration signal. Further, the communication unit 19 receives the vibration signal (the second vibration signal) generated according to the tapping input of the other party by the wristband-type terminal 1-2. Thus, the wristband-type terminal 1-1 vibrates according to the received vibration signal through the vibrating unit 16.

Further, the communication unit 19 transmits the state signal (the first state signal) generated according to the state of the user through the state signal generating unit 155 to the wristband-type terminal 1-2. Thus, the wristband-type terminal 1-2 notifies the other party of the state of the user according to the received state signal through the display of the avatar 6 or the lighting of the LED 3. Further, the communication unit 19 receives the state signal (the second state signal) generated according to the state of the other party by the wristband-type terminal 1-2. Thus, the wristband-type terminal 1-1 notifies the user of the state of the other party according to the received state signal through the display of the avatar 6 or the lighting of the LED 3.

Further, the communication unit 19 receives the incoming call type indicating whether or not the tapping vibration according to the vibration signal (the first vibration signal) generated according to the tapping input of the user by the vibration signal generating unit 156 has been transmitted to the other party from the wristband-type terminal 1-2. Thus, the user can understand whether or not the tapping vibration has been transmitted to the other party, that is, whether or not there was a missed incoming call. Further, the communication unit 19 transmits the incoming call type indicating whether or not the tapping vibration according to the vibration signal (the second vibration signal) generated according to the tapping input of the other party by the wristband-type terminal 1-2 has been transmitted to the user to the wristband-type terminal 1-1. Thus, the other party can understand whether or not the tapping vibration has been transmitted to the user, that is, whether or not there was a missed incoming call. Hereinafter, a vibration signal transmitted by the communication unit 19 is also referred to as "tapping notification."

Further, the communication unit 19 transmits the vibration pattern information (the first vibration pattern information) generated by the vibration pattern generating unit 154 to the wristband-type terminal 1-2. Similarly, the communication unit 19 receives the vibration pattern information (the second vibration pattern information) generated by the wristband-type terminal 1-2 from the wristband-type terminal 1-2.

Further, the communication unit 19 transmits the determination result obtained by the pattern determining unit 151 to the wristband-type terminal 1-2. Thus, the other party can understand whether or not the tapping input has been performed at the same timing as the user or the tapping communication end timing. Similarly, the communication unit 19 receives the determination result obtained by the pattern determining unit 151 of the wristband-type terminal 1-2 from the wristband-type terminal 1-2.

(Network 7)

The network 7 is a wired or wireless transmission path of information transmitted from a device connected to the network 7. For example, the network 7 is configured with the Internet such as a Wireless Local Area Network (WLAN) or Wireless Fidelity (Wi-Fi) (a registered trademark). In addition, the network 7 is configured with a public telephone network such as 3G/LTE including an exchange station and a base station.

The internal configuration of the wristband-type terminal 1 according to the present embodiment has been described above. Next, communication systems according to embodiments of the present disclosure will be described.

2-2. Embodiments 2-2-1. First Embodiment

The present embodiment is a form in which the tapping communication is performed between the two associated wristband-type terminals 1. An operation process of the communication system according to the present embodiment will be described below with reference to FIG. 5.

Figure 5:
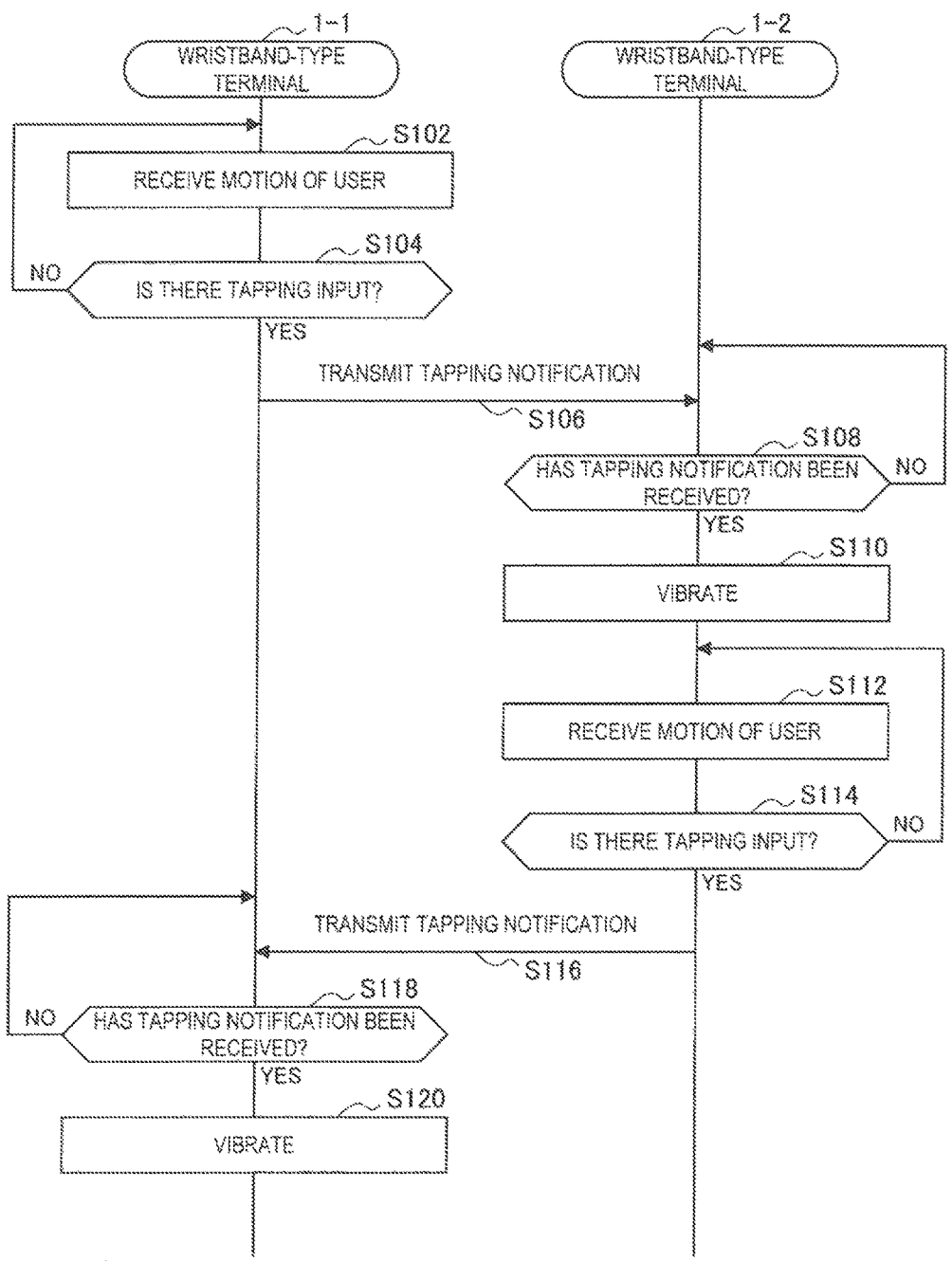
FIG. 5 is a sequence diagram illustrating an operation of a communication system according to a first embodiment.

FIG. 5 is a sequence diagram illustrating an operation of the communication system according to a first embodiment. As illustrated in FIG. 5, first, in step S102, the wristband-type terminal 1-1 receives a motion of the user. More specifically, the sensor unit 13 detects the motion of the user through the vibration sensor, the pressure sensor, or the like.

Then, in step S104, the wristband-type terminal 1-1 determines whether or not there is the tapping input. More specifically, the motion determining unit 152 determines whether or not there is the tapping input based on whether or not the amplitude of the vibration waveform obtained by the sensor unit 13 has exceeded a threshold value, whether or not a pattern of a period is identical to a previously stored pattern, or the like.

When it is determined that there is the tapping input (YES in S104), in step S106, the wristband-type terminal 1-1 transmits the tapping notification to the wristband-type terminal 1-2. More specifically, the communication unit 19 transmits the vibration signal generated according to the tapping input by the vibration signal generating unit 156 to the wristband-type terminal 1-2. Further, when it is determined that there is no tapping input (NO in S104), the process returns to step S102.

Then, in step S108, the wristband-type terminal 1-2 determines whether or not the tapping notification has been received. More specifically, the control unit 15 determines whether or not the vibration signal has been received from the wristband-type terminal 1-1.

When the tapping notification is determined to have been received (YES in S108), in step S110, the wristband-type terminal 1-2 vibrates. More specifically, the vibrating unit 16 vibrates according to the vibration signal received from the wristband-type terminal 1-1 by the communication unit 19. Further, when the tapping notification is determined not to have been received (NO in S108), the process returns to step S108.

Then, in step S112, the wristband-type terminal 1-2 receives a motion of the user.

Then, in step S114, the wristband-type terminal 1-2 determines whether or not there is the tapping input.

When it is determined that there is the tapping input (YES in S114), in step S116, the wristband-type terminal 1-2 transmits the tapping notification to the wristband-type terminal 1-1. Further, when it is determined that there is no tapping input (NO in S114), the process returns to step S112.

Then, in step S118, the wristband-type terminal 1-1 determines whether or not the tapping notification has been received.

When the tapping notification is determined to have been received (YES in S118), in step S120, the wristband-type terminal 1-1 vibrates. Further, when the tapping notification is determined not to have been received (NO in S118), the process returns to step S118.

The operation process of the communication system according to the present embodiment has been described above.

2-2-2. Second Embodiment

The present embodiment is a form in which a notification of a missed incoming call is given to the user when the user is not wearing the wristband-type terminal 1 at the time of the tapping communication. An operation process of the communication system according to the present embodiment will be described below with reference to FIGS. 6 and 7.

Figure 6:
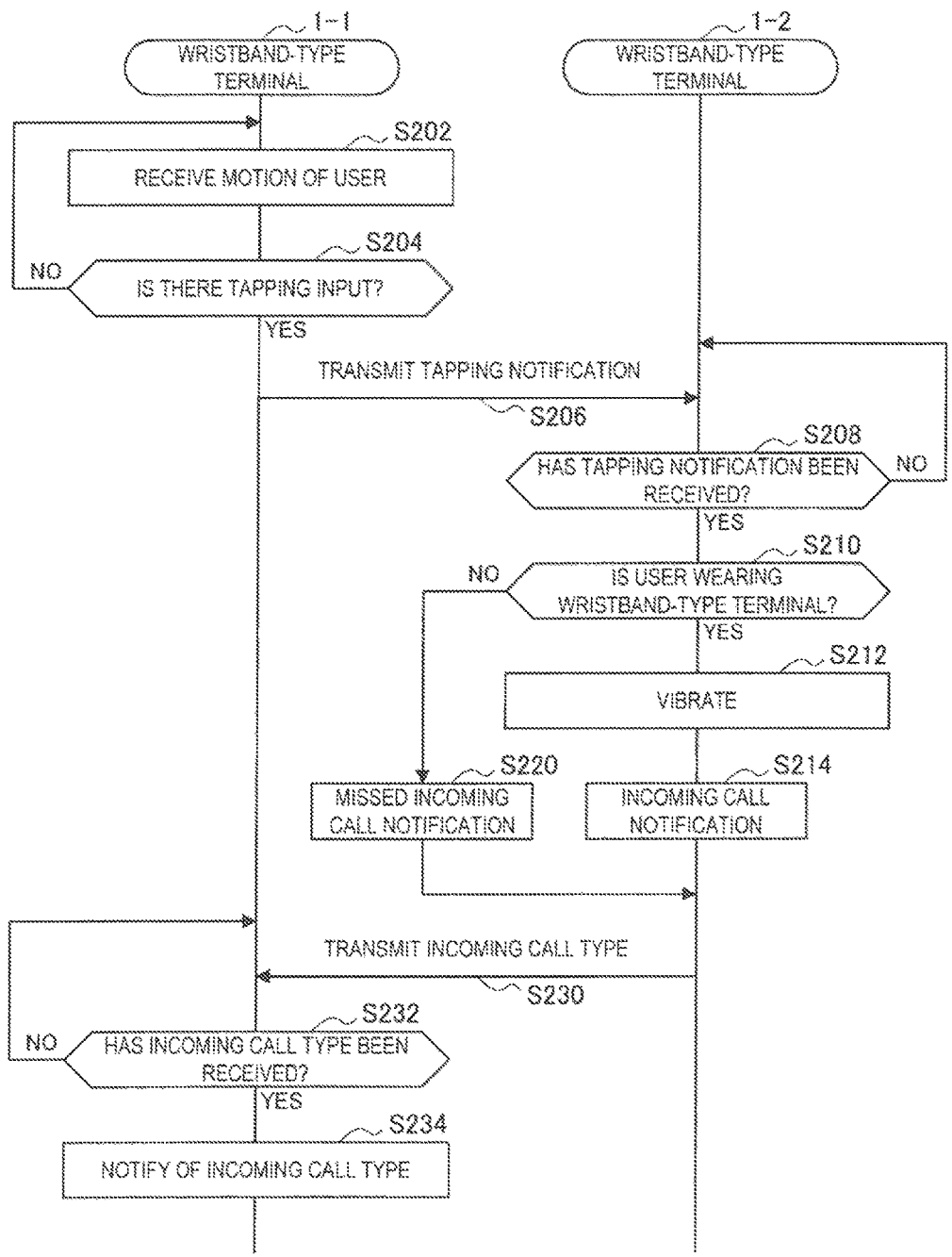
FIG. 6 is a sequence diagram illustrating an operation of a communication system according to a second embodiment.

FIG. 6 is a sequence diagram illustrating an operation of the communication system according to a second embodiment. As illustrated in FIG. 6, fit, in step S202, the wristband-type terminal 1-1 receives a motion of the user.

Then, in step S204, the wristband-type terminal 1-1 determines whether or not there is the tapping input.

When it is determined that there is the tapping input (YES in S204), in step S206, the wristband-type terminal 1-1 transmits the tapping notification to the wristband-type terminal 1-2. Further, when it is determined that there is no tapping input (NO in S204), the process returns to step S202.

Then, in step S208, the wristband-type terminal 1-2 determines whether or not the tapping notification has been received.

When the tapping notification is determined to have been received (YES in S208), in step S210, the wristband-type terminal 1-2 determines whether or not the user (the other party from the perspective of the user of the wristband-type terminal 1-1) is wearing the wristband-type terminal 1-2. More specifically, the sensor unit 13 detects whether or not the user is wearing the wristband-type terminal 1-2 through the touch sensor, the illuminance sensor, the clinical thermometer, or the pulsimeter installed in the band section 4.

Further, when the tapping notification is determined not to have been received (NO in S208), the process returns to step S208.

When the user is determined to be wearing the wristband-type terminal 1-2 (YES in S210), in step S212, the wristband-type terminal 1-2 vibrates.

Then, in step S214, the wristband-type terminal 1-2 give the incoming call notification. More specifically, the notifying unit 17 notifies the user (the other party from the perspective of the user of the wristband-type terminal 1-1) of information indicating that the tapping vibration has been performed based on the tapping notification from the wristband-type terminal 1-1. For example, the notifying unit 17 displays a mark indicating an incoming call or the avatar 6 indicating the user of the wristband-type terminal 1-1 serving as the transmission source of the vibration signal or turns on the LED 3. The wristband-type terminal 1-2 lets the user know a person from whom the tapping vibration has been received through the incoming call notification and thus can improve intimacy between persons who have performed the tapping communication.

On the other hand, when the user is determined not to be wearing the wristband-type terminal 1-2 (NO in S210), in step S220, the wristband-type terminal 1-2 gives the missed incoming call notification. More specifically, the notifying unit 17 notifies the user (the other party from the perspective of the user of the wristband-type terminal 1-1) of information indicating that there was the tapping notification from the wristband-type terminal 1-1. For example, the notifying unit 17 displays a mark indicating a missed incoming call or the avatar 6 indicating the user of the wristband-type terminal 1-1 serving as the transmission source of the vibration signal and turns on the LED 3. The wristband-type terminal 1-2 can encourage the user to perform the tapping input according to the missed incoming call notification and promote communication.

Thereafter, in step S230, the wristband-type terminal 1-2 transmits information indicating the incoming call type (the missed incoming call/the incoming call) to the wristband-type terminal 1-1. More specifically, the communication unit 19 transmits information indicating whether or not step S214 has been performed or whether or not step S220 has been performed through the notifying unit 17 to the wristband-type terminal 1-1.

Then, in step S232, the wristband-type terminal 1-1 determines whether or not the incoming call type has been received.

When the incoming call type is determined to have been received (YES in S232), in step S234, the wristband-type terminal 1-1 notifies the user of the incoming call type. More specifically, the notifying unit 17 notifies the user of information indicating whether or not the tapping input of the user in step S202 has been transmitted to the other party in step S214 or whether or not the missed incoming call has been received, but the tapping input has not been transmitted to the other party yet in step S220 based on the received incoming call type. Further, when the incoming call type is determined not to have been received (NO in S232), the process returns to step S232.

The operation of the communication system when there is a missed incoming call has been described above. Next, an operation of the wristband-type terminal 1-2 after the missed incoming call notification is performed in step S220 will be described in detail with reference to FIG. 7.

Figure 7:
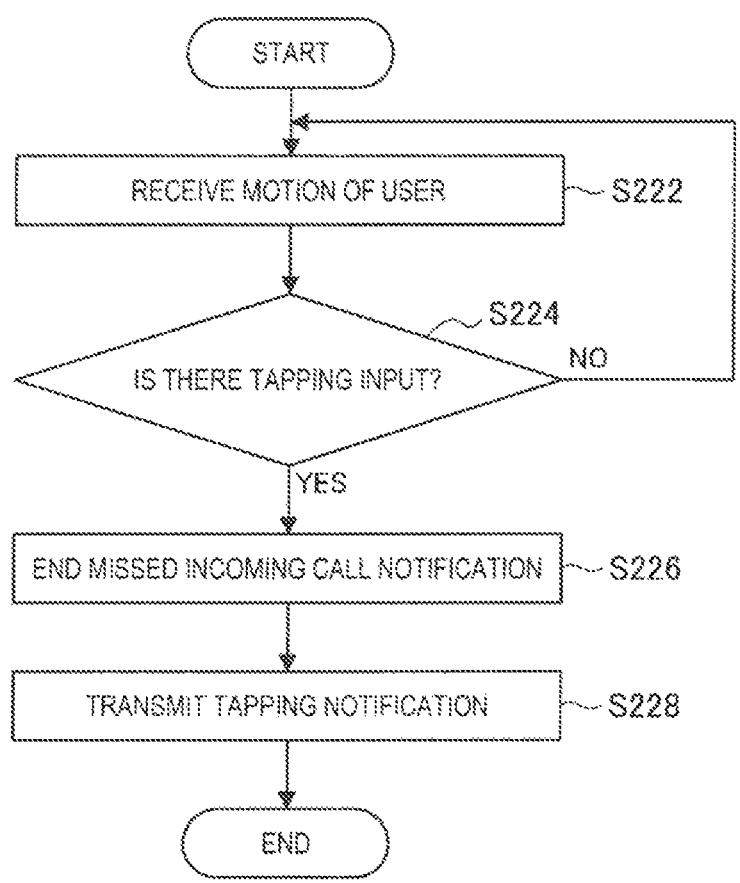
FIG. 7 is a flowchart illustrating an operation of a wristband-type terminal according to a second embodiment.

FIG. 7 is a flowchart illustrating an operation of the wristband-type terminal 1-2 according to the second embodiment. As illustrated in FIG. 7, first, in step S222, the wristband-type terminal 1-2 receives a motion of the user.

Then, in step S224, the wristband-type terminal 1-2 determines whether or not there is the tapping input.

When it is determined that there is the tapping input (YES in S224), in step S226, the wristband-type terminal 1-2 ends the missed incoming call notification. Further, when it is determined that there is no tapping input (NO in S224), the process returns to step S222.

Then, in step S228, the wristband-type terminal 1-2 transmits the tapping notification to the wristband-type terminal 1-1.

The operation process of the communication system according to the present embodiment has been described above.

2-2-3. Third Embodiment

The present embodiment is a form in which the tapping communication using the state notification as the trigger is performed. The operation process of the communication system according to the present embodiment will be described below with reference to FIG. 8.

Figure 8:
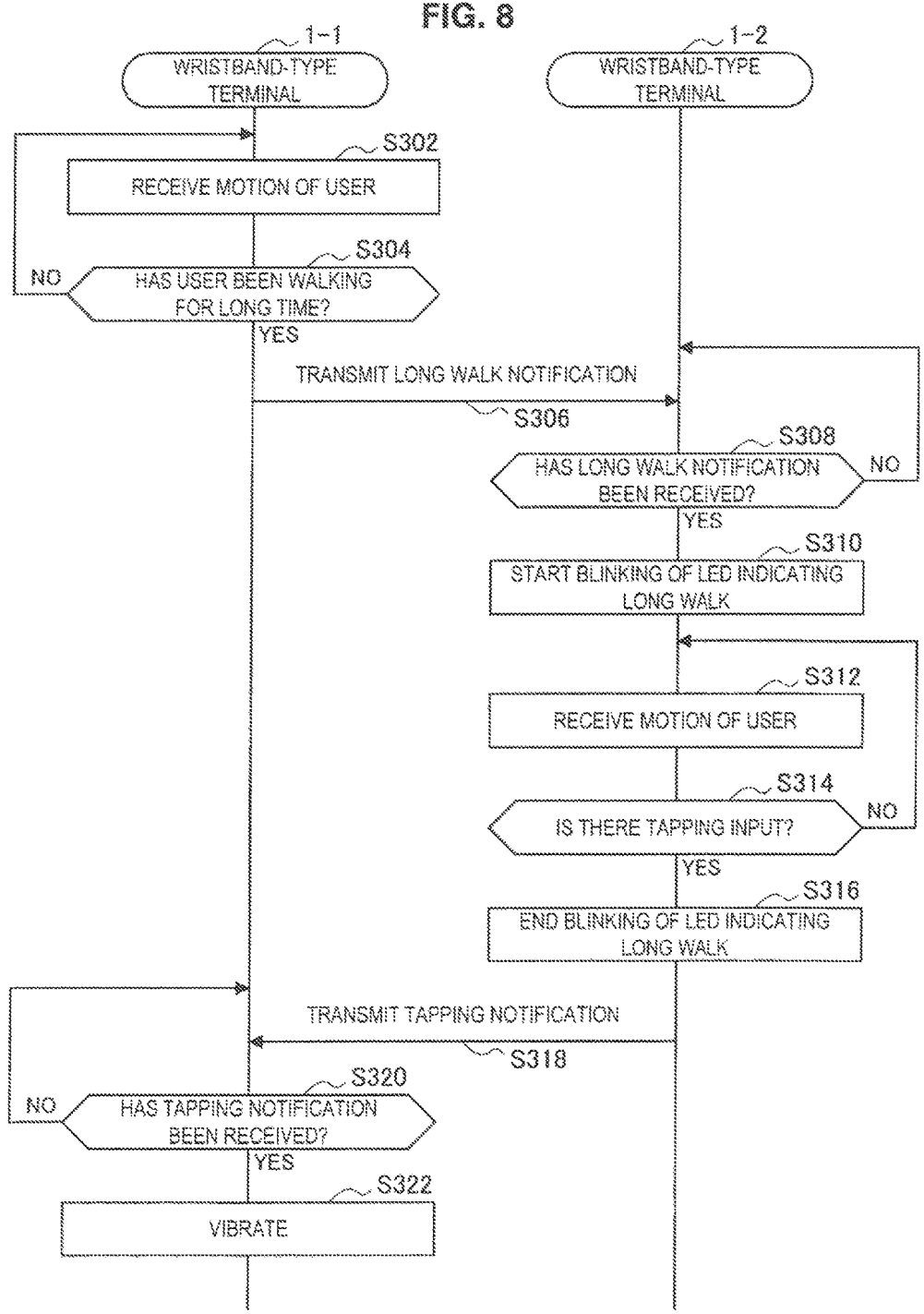
FIG. 8 is a sequence diagram illustrating an operation of a communication system according to a third embodiment.

FIG. 8 is a sequence diagram illustrating an operation of the communication system according to a third embodiment. More specifically, FIG. 8 illustrates an operation process of the tapping communication using the state notification as the trigger in the wristband-type terminal 1 having the external configuration described above with reference to FIG. 2, that is, including the LED 3.

As illustrated in FIG. 8, first, in step S302, the wristband-type terminal 1-1 receives a motion of the user.

Then, in step S304, the wristband-type terminal 1-1 determines whether or not the user has been walking for a long time. More specifically, the state determining unit 153 determines, for example, whether or not the user has been continuously walking for three hours or more based on the sensing result such as the acceleration, the vibration, and the time information acquired by the sensor unit 13.

When the user is determined to have been walking for a long time (YES in S304), in step S306, the wristband-type terminal 1-1 transmits a long walk notification indicating that the user has been walking for a long time to the wristband-type terminal 1-2. More specifically, the communication unit 19 transmits a state signal indicating that the user has been walking for a long time, which is generated by the state signal generating unit 155, to the wristband-type terminal 1-2. Further, when the user is determined not to have been walking for a long time (NO in S304), the process returns to step S302.

Then, in step S308, the wristband-type terminal 1-2 determines whether or not the long walk notification has been received.

When the long walk notification is determined to have been received (YES in S308), in step S310, the wristband-type terminal 1-2 starts blinking of the LED 3 indicating that the user has been walking for a long time. Thus, it is possible to let the user of the wristband-type terminal 1-2 know that the user of the wristband-type terminal 1-1 has been walking for a long time and encourage communication by the tapping vibration. Further, when the long walk notification is determined not to have been received (NO in S308), the process returns to step S308.

Then, in step S312, the wristband-type terminal 1-2 receives a motion of the user.

Then, in step S314, the wristband-type terminal 1-2 determines whether or not there is the tapping input.

When it is determined that there is the tapping input (YES in S314), in step S316, the wristband-type terminal 1-2 ends blinking of the LED 3 indicating that the user has been walking for a long time. Further, when it is determined that there is no tapping input (NO in S314), the process returns to step S312.

Then, in step S318, the wristband-type terminal 1-2 transmits the tapping notification to the wristband-type terminal 1-1.

Then, in step S320, the wristband-type terminal 1-1 determines whether or not the tapping notification has been received.

When the tapping notification is determined to have been received (YES in S320), in step S322, the wristband-type terminal 1-1 vibrates. Further, when the tapping notification is determined not to have been received (NO in S320), the process returns to step S320.

The operation process of the tapping communication using the state notification as the trigger in the wristband-type terminal 1 including the LED 3 has been described above. Next, an operation process of the tapping communication using the state notification as the trigger in the wristband-type terminal 1 having the external configuration described above with reference to FIG. 3, that is, including the display section 5, will be described with reference to FIG. 9.

Figure 9:
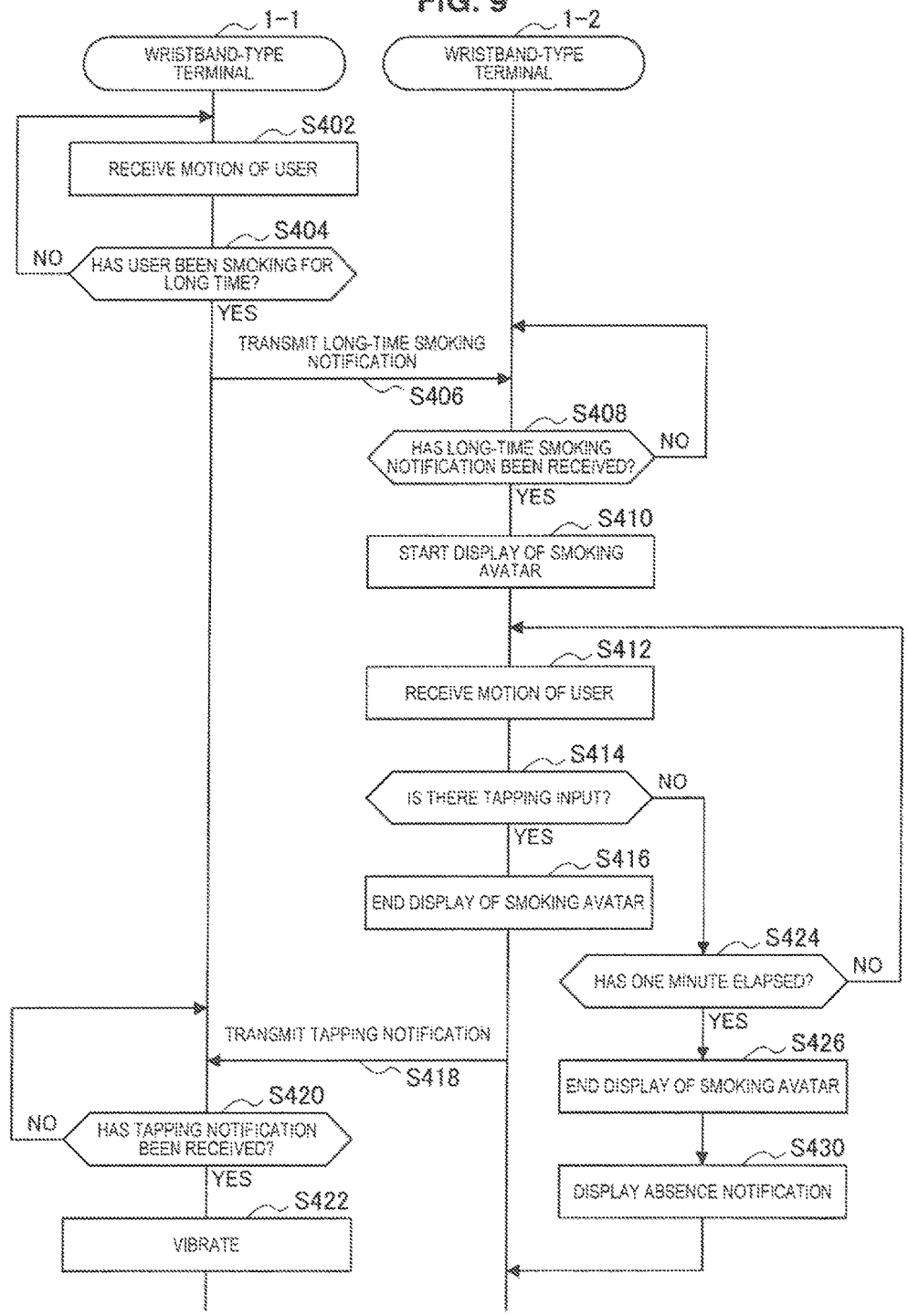
FIG. 9 is a sequence diagram illustrating an operation of a communication system according to a third embodiment.

FIG. 9 is a sequence diagram illustrating an operation of the communication system according to a third embodiment. As illustrated in FIG. 9, first, in step S402, the wristband-type terminal 1-1 receives a motion of the user.

Then, in step S404, the wristband-type terminal 1-1 determines whether or not the user has been smoking for a long time. More specifically, the state determining unit 153 determines, for example, whether or not the user has been continuously smoking for one hour or more based on the sensing result such as the acceleration, the vibration, or the time information acquired by the sensor unit 13.

When the user is determined to have been smoking for a long time (YES in S404), in step S406, the wristband-type terminal 1-1 transmits a long-time smoking notification indicating that the user has been smoking for a long time to the wristband-type terminal 1-2. More specifically, the communication unit 19 transmits a state signal indicating that the user has been smoking for a long time, which is generated by the state signal generating unit 155 to the wristband-type terminal 1-2. Further, when the user is determined not to have been smoking for a long time (NO in S404), the process returns to step S402.

Then, in step S408, the wristband-type terminal 1-2 determines whether or not the long-time smoking notification has been received.

When the long-time smoking notification is determined to have been received (YES in S408), in step S410, the wristband-type terminal 1-2 starts to display a smoking avatar indicating that the user has been smoking for a long time. More specifically, the display section 5 displays a form in which the avatar 6 indicating the user of the wristband-type terminal 1-1 is smoking as illustrated in FIG. 3. Thus, it is possible to let the user of the wristband-type terminal 1-2 know that the user of the wristband-type terminal 1-1 has been smoking for a long time and encourage communication by the tapping vibration. Further, when the long-time smoking notification is determined not to have been received (NO in S408), the process returns to step S408.

Then, in step S412, the wristband-type terminal 1-2 receives a motion of the user.

Then, in step S414, the wristband-type terminal 1-2 determines whether or not there is the tapping input.

When it is determined that there is the tapping input (YES in S414), in step S416, the wristband-type terminal 1-2 ends the display of the smoking avatar indicating that the user has been smoking for a long time.

Then, in step S418, the wristband-type terminal 1-2 transmits the tapping notification to the wristband-type terminal 1-1.

Then, in step S420, the wristband-type terminal 1-1 determines whether or not the tapping notification has been received.

When the tapping notification is determined to have been received (YES in S420), in step S422, the wristband-type terminal 1-1 vibrates. Further, when the tapping notification is determined not to have been received (NO in S420), the process returns to step S420.

On the other hand, when the tapping input is determined not to have been performed in step S414 (NO in S414), in step S424, the wristband-type terminal 1-2 determines whether or not one minute has elapsed.

When one minute is determined not to have elapsed (NO in S424), the process returns to step S412. On the other hand, when one minute is determined to have elapsed (YES in S424), in step S426, the wristband-type terminal 1-2 ends the display of the smoking avatar indicating that the user has been smoking for a long time.

Then, in step S430, the wristband-type terminal 1-2 gives an absence notification indicating that the state notification from the wristband-type terminal 1-1 has been ignored to the user (the other party from the perspective of the user of the wristband-type terminal 1-1). The wristband-type terminal 1-2 encourages the user to perform the tapping input through the absence notification and promotes communication.

The operation process of the tapping communication using the state notification as the trigger in the wristband-type terminal 1 including the display section 5 has been described above. Next, an operation of the wristband-type terminal 1-2 after the absence notification is given in step S430 will be described in detail with reference to FIG. 10.

Figure 10:
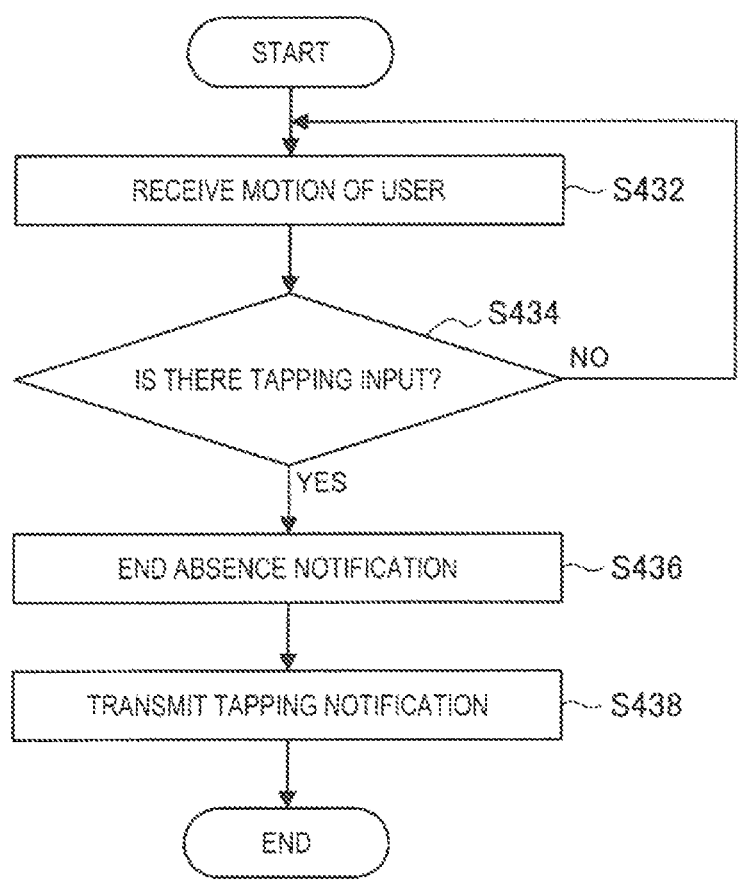
FIG. 10 is a flowchart illustrating an operation of a wristband-type terminal according to a third embodiment.

FIG. 10 is a flowchart illustrating an operation of the wristband-type terminal 1-2 according to a third embodiment. As illustrated in FIG. 10, first, in step S432, the wristband-type terminal 1-2 receives a motion of the user.

Then, in step S434, the wristband-type terminal 1-2 determines whether or not there is the tapping input.

When it is determined that there is the tapping input (YES in S434), in step S436, the wristband-type terminal 1-2 ends display of the absence notification. Further, when it is determined that there is no tapping input (NO in S434), the process returns to step S432.

Then, in step S438, the wristband-type terminal 1-2 transmits the tapping notification to the wristband-type terminal 1-1.

The operation process of the communication system according to the present embodiment has been described above.

2-2-4. Fourth Embodiment

The present embodiment is a form in which, after the tapping communication using the state notification as the trigger is performed, a notification indicating what is used as a trigger for transmission of the tapping vibration is given to a side to which the tapping vibration is transmitted. An operation process of the communication system according to the present embodiment will be described below with reference to FIG. 11.

Figure 11:
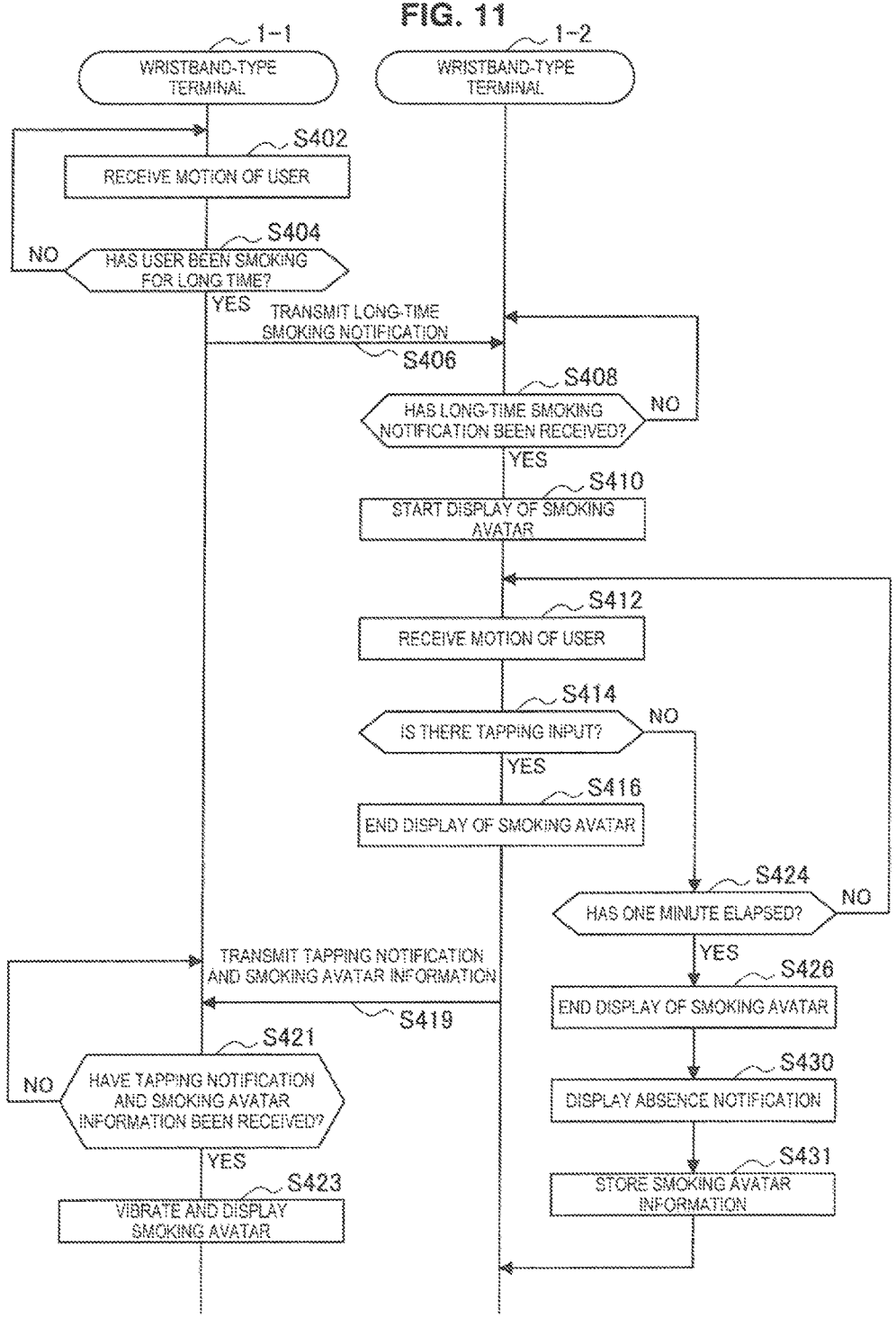
FIG. 11 is a sequence diagram illustrating an operation of a communication system according to a fourth embodiment.

FIG. 11 is a sequence diagram illustrating an operation of the communication system according to a fourth embodiment. As illustrated in FIG. 11, in steps S402 to S416, the communication system according to the present embodiment operates as described above with reference to FIG. 9.

After step S416, in step S419, the wristband-type terminal 1-2 transmits smoking avatar information to the wristband-type terminal 1-1 together with the tapping notification. Here, the smoking avatar information is information indicating that the user of the wristband-type terminal 1-2 (the other party viewed from the user of the wristband-type terminal 1-1) has performed the tapping input using the fact that the user of the wristband-type terminal 1-1 has been smoking for a long time as the trigger.

Then, in step S421, the wristband-type terminal 1-1 determines whether or not the tapping notification and the smoking avatar information have been received.

When the tapping notification and the smoking avatar information are determined to have been received (YES in S421), in step S423, the wristband-type terminal 1-1 displays the smoking avatar information while vibrating. More specifically, the vibrating unit 16 vibrates according to the vibration signal received from the wristband-type terminal 1-2 through the communication unit 19. Further, the notifying unit 17 causes information indicating that the tapping vibration has been transmitted from the wristband-type terminal 1-2 to be displayed on the display section 5 using the fact that the user was smoking for a long time as the trigger. For example, the notifying unit 17 displays an avatar indicating that the user of the wristband-type terminal 1-1 is smoking. Thus, the user can understand that the other party is worrying about his/her smoking, and thus more intimate communication is implemented. Further, when the tapping notification and the smoking avatar information are determined not to have been received (NO in S421), the process returns to step S421.

On the other hand, in step S414, when the tapping input is determined not to have been performed (NO in S414), in steps S424 to S430, the communication system according to the present embodiment operates as described above with reference to FIG. 9.

After step S430, in step S431, the wristband-type terminal 1-2 stores the smoking avatar information.

The operation process of the tapping communication in which a notification indicating what is used as the trigger for transmission of the tapping vibration is given has been described above.

The example in which the smoking avatar information is received from the wristband-type terminal 1-2 as the information indicating the long-time smoking that is the state of the user serving as the trigger in step S419 has been described, but the present embodiment is not limited to this technique. For example, in step S406, the wristband-type terminal 1-1 transmits the long-time smoking notification and stores information indicating that the long-time smoking notification has been transmitted. Then, when the tapping notification is received from the wristband-type terminal 1-2 later, the wristband-type terminal 1-1 may display the smoking avatar information in step S423 based on the information indicating that the long-time smoking notification has been transmitted in the past.

Next, an operation of the wristband-type terminal 1-2 after the smoking avatar information is stored in step S431 will be described in detail with reference to FIG. 12.

Figure 12:
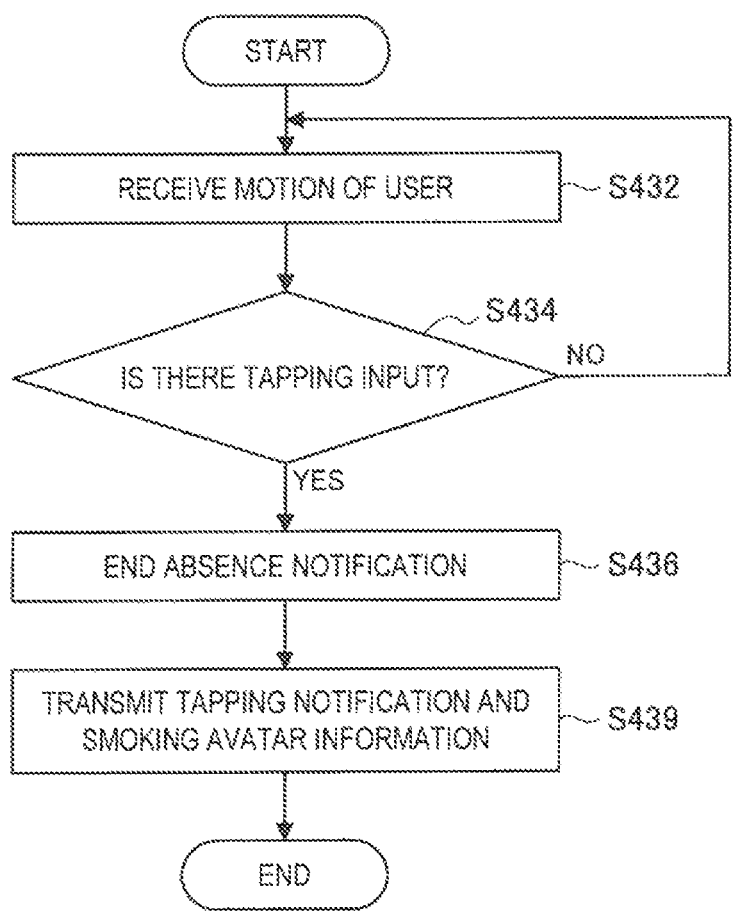
FIG. 12 is a flowchart illustrating an operation of a wristband-type terminal according to a fourth embodiment.

FIG. 12 is a flowchart illustrating an operation of the wristband-type terminal 1-2 according to a fourth embodiment. As illustrated in FIG. 12, in steps S432 to S436, the communication system according to the present embodiment operates as described above with reference to FIG. 10.

After step S436, in step S439, the wristband-type terminal 1-2 transmits the tapping notification and the smoking avatar information to the wristband-type terminal 1-1. As described above with reference to FIG. 11, the user of the wristband-type terminal 1-1 can understand that the user of the wristband-type terminal 1-2 is worrying about his/her smoking based on the smoking avatar information, and thus more intimate communication is implemented.

The operation process of the communication system according to the present embodiment has been described above.

2-2-5. Fifth Embodiment

The present embodiment is a form in which the user is set as the other party of the tapping communication. First, an overview of the present embodiment will be described with reference to FIG. 13.

Figure 13:
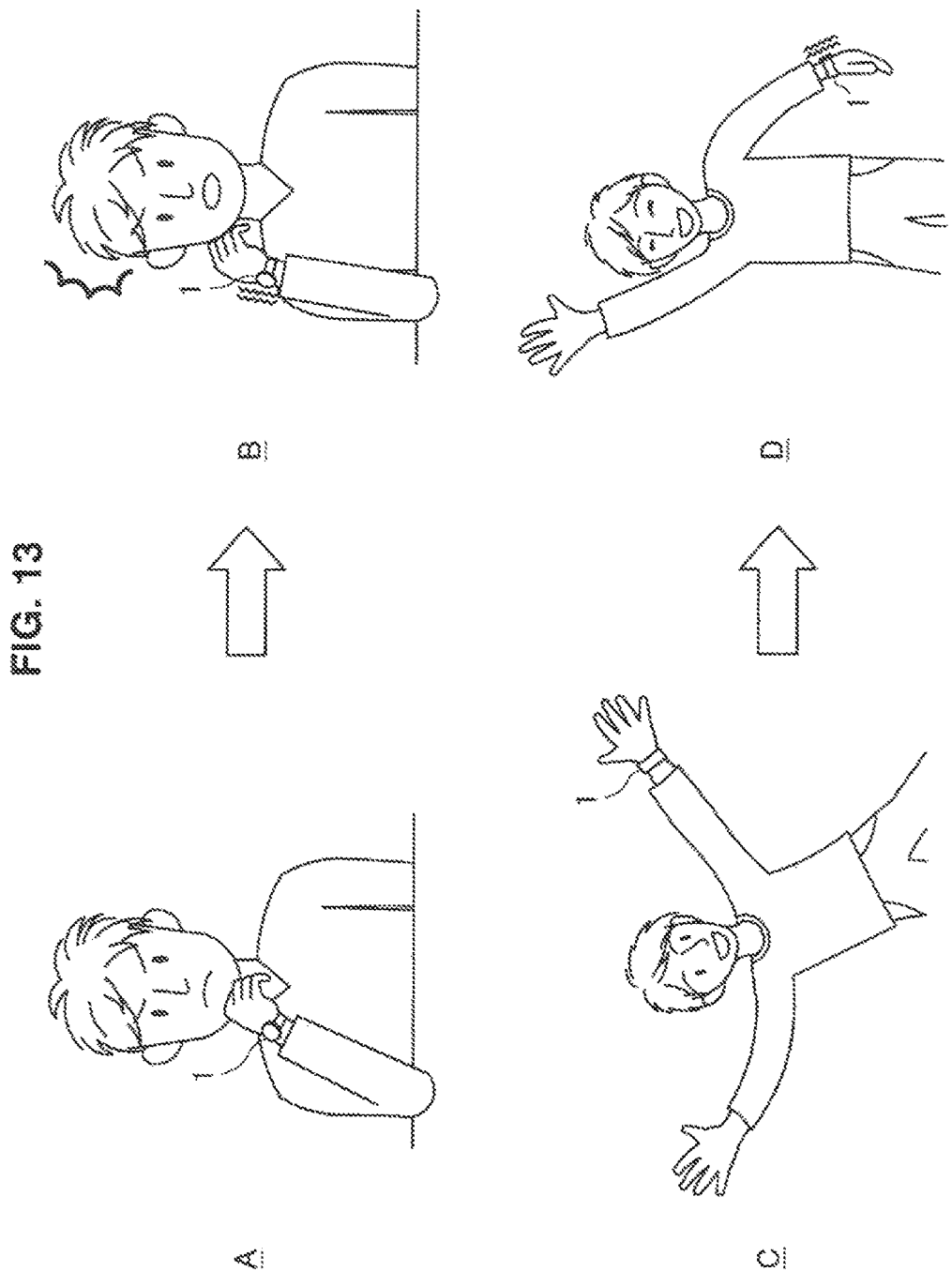
FIG. 13 is a diagram illustrating an overview of a wristband-type terminal according to a fifth embodiment.

FIG. 13 is a diagram illustrating an overview of the wristband-type terminal 1 according to the fifth embodiment. As illustrated in FIG. 13A, the user wearing the wristband-type terminal 1 is irritated. At this time, the user stores such a feeling of irritation in the wristband-type terminal 1. For example, the wristband-type terminal 1 stores the biometric information such as a pulse, sweating, or a body temperature of the user at that time of the feeling of irritation. Then, when the biometric information indicating that the user is irritated similarly to FIG. 13A is detected as illustrated in FIG. 13B, the wristband-type terminal 1 performs the tapping vibration. Thus, the user can snap out of and controls the feeling of irritation.

Further, as illustrated in FIG. 13C, the user wearing the wristband-type terminal 1 is happy. At this time, the user stores the happy feeling in the wristband-type terminal 1. Then, when the user is detected to be happy similarly to FIG. 13C as illustrated in FIG. 13D, the wristband-type terminal 1 performs the tapping vibration. Thus, the user can recall the happy emotion from the past and double his/her happiness. An operation process of the wristband-type terminal 1 according to the present embodiment will be specifically described below with reference to FIG. 14.

Figure 14:
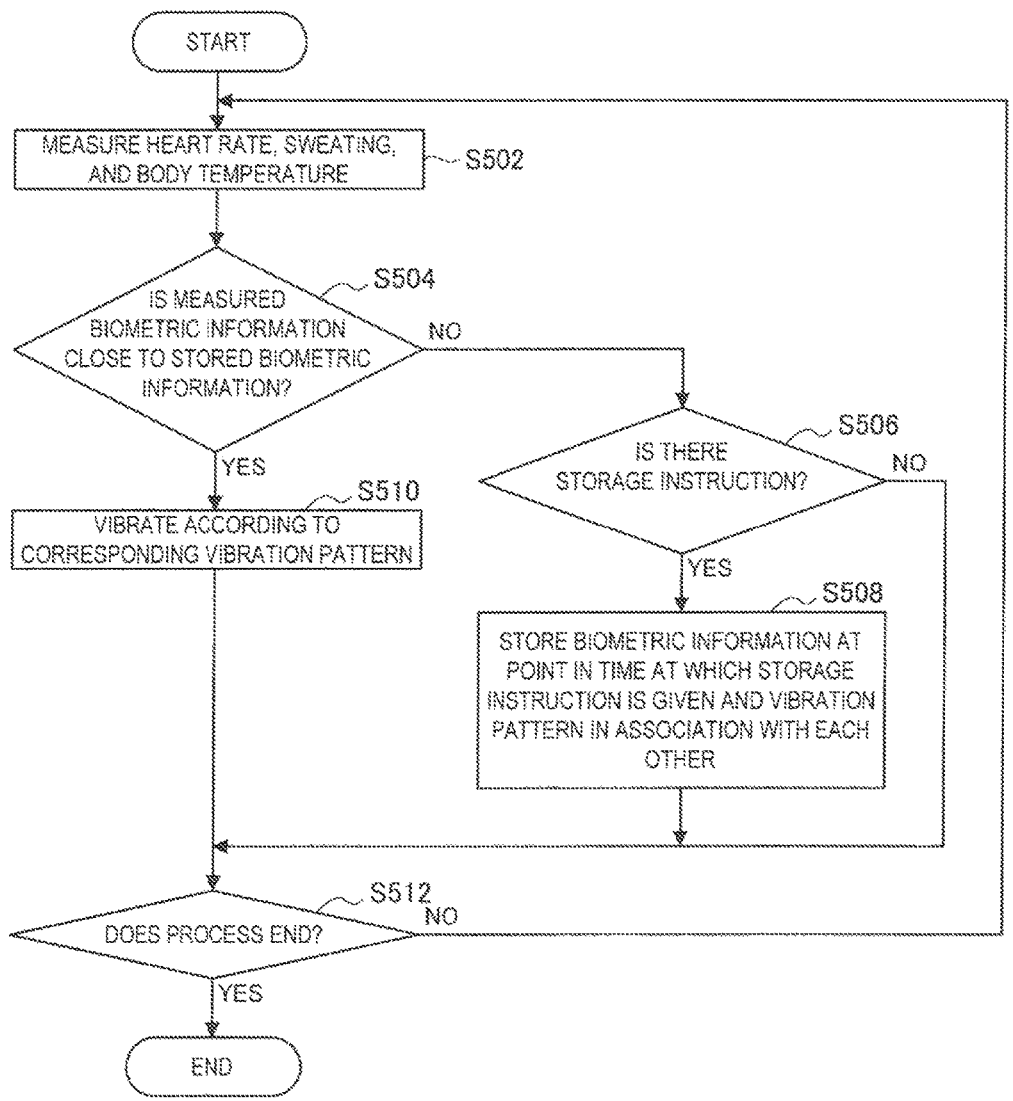
FIG. 14 is a flowchart illustrating an operation of the wristband-type terminal according to the fifth embodiment.

FIG. 14 is a flowchart illustrating an operation of the wristband-type terminal 1 according to the fifth embodiment. As illustrated in FIG. 14, first, in step S502, the sensor unit 13 measures the biometric information such as the heart rate, the sweating, or the body temperature of the user.

Then, in step S504, the control unit 15 determines whether or not the biometric information measured by the sensor unit 13 is close to, that is, the same as or similar to, the biometric information stored in the storage unit 18. More specifically, the control unit 15 searches for the biometric information in which a numerical value of the heart rate, the sweating, or the body temperature is within a predetermined threshold value from a numerical value of the heart rate, the sweating, or the body temperature measured by the sensor unit 13 from the storage unit 18.

When the measured biometric information is determined not to be close to the stored biometric information (NO in S504), in step S506, the wristband-type terminal 1 determines whether or not there was a storage instruction to instruct storage of a feeling. More specifically, the control unit 15 determines whether or not a storage instruction button (not illustrated) has been pushed by the user. In addition, the control unit 15 may determine that there was the storage instruction when there was the tapping input.

When it is determined that there was the storage instruction (YES in S506), in step S508, the storage unit 18 stores the biometric information at a point in time at which the storage instruction is given and a vibration pattern selected by the user among preset vibration patterns in association with each other. Thereafter, the process proceeds to step S512 which will be described later. Further, the process also proceeds to step S512 to be described later when it is determined that there was no storage instruction (NO in S506).

On the other hand, when the measured biometric information is determined to be close to the stored biometric information in step S504 (YES in S504), in step S510, the vibrating unit 16 vibrates according to the corresponding vibration pattern. More specifically, the vibrating unit 16 vibrates according to the vibration pattern that has previously been stored in the storage unit 18 in association with the biometric information determined to be close to the measured biometric information in step S508.

Then, in step S512, the control unit 15 determines whether or not the process ends. For example, the control unit 15 determines whether or not the process ends based on the presence of absence of an end instruction given by the user. When the process is determined to end (YES in SS 512), the process ends, whereas when the process is determined not to end (NO in S512), the process returns to step S502.

The operation process of the wristband-type terminal 1 according to the present embodiment has been described above.

2-2-6. Sixth Embodiment

The present embodiment is a form in which a notification indicating whether or not the user of the wristband-type terminal 1-1 and the user of the wristband-type terminal 1-2 have performed the tapping input at the same timing is given to the user. For example, the present embodiment is applied to a game of matching a tapping input timing between friends or a couple. An operation mode in which the communication system according to the present embodiment operates as the game of matching a tapping input timing is also referred to as a "synchronization mode." An operation process of the communication system according to the present embodiment will be described below with reference to FIGS. 15 to 17.

Figure 15:
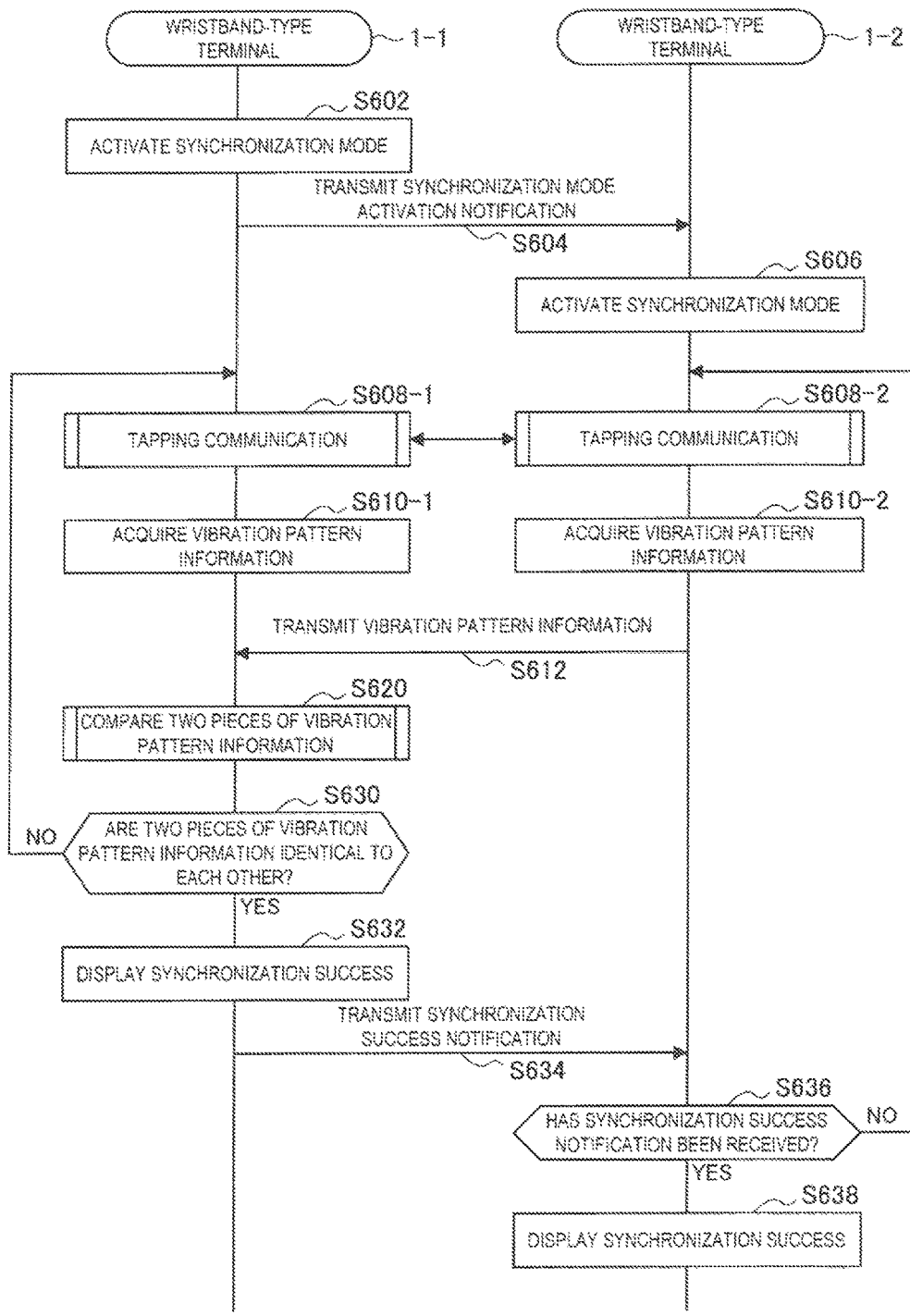
FIG. 15 is a sequence diagram illustrating an operation of a communication system according to a sixth embodiment.

FIG. 15 is a sequence diagram illustrating an operation of the communication system according to a sixth embodiment. As illustrated in FIG. 15, in step S602, the wristband-type terminal 1-1 activates the synchronization mode.

Then, in step S604, the wristband-type terminal 1-1 transmits a synchronization mode activation notification to the wristband-type terminal 1-2.

Then, in step S606, the wristband-type terminal 1-2 activates the synchronization mode based on the received synchronization mode activation notification.

Then, in steps S608-1 and S608-2, the wristband-type terminals 1-1 and 1-2 perform the tapping communication. The tapping communication has been described above with reference to FIG. 5, and thus a detailed description thereof is omitted here.

Then, in step S610-1, the wristband-type terminal 1-1 acquires the vibration pattern information. More specifically, the vibration pattern generating unit 154 generates the vibration pattern information indicating the vibration pattern of the tapping input that is performed by the user and detected by the sensor unit 13. In step S610-2, similarly, the wristband-type terminal 1-2 acquires the vibration pattern information.

Then, in step S612, the wristband-type terminal 1-2 transmits the vibration pattern information acquired in step S610-2 to the wristband-type terminal 1-1.

Then, in step S620, the wristband-type terminal 1-1 compares the vibration pattern information acquired in the wristband-type terminal 1-1 with the vibration pattern information acquired in the wristband-type terminal 1-2. This process will be described in detail later with reference to FIG. 16, and thus a description is omitted here.

Then, in step S630, the wristband-type terminal 1-1 determines whether or not the two pieces of vibration pattern information are identical to each other. More specifically, the control unit 15 determines whether or not the two pieces of vibration pattern information are identical to each other with reference to the determination result obtained by the pattern determining unit 151 in step S620 which will be described in detail.

When the two pieces of vibration pattern information are determined to be identical to each other (YES in S630), in step S632, the wristband-type terminal 1-1 displays information indicating synchronization success. More specifically, the notifying unit 17 causes a message indicating the synchronization success to be displayed on the display section 5 or causes the LED 3 indicating the synchronization success to blink. Further, when the two pieces of vibration pattern information are determined not to be identical to each other (NO in S630), the process returns to step S608-1.

Then, in step S634, the wristband-type terminal 1-1 transmits a synchronization success notification to the wristband-type terminal 1-2.

Then, in step S636, the wristband-type terminal 1-2 determines whether or not the synchronization success notification has been received.

When the synchronization success notification is determined to have been received (YES in S636), in step S638, the wristband-type terminal 1-2 displays information indicating the synchronization success. Further, when the synchronization success notification is determined not to have been received (NO in S636), the process returns to step S608-2.

The operation process of the communication system according to the present embodiment in the synchronization mode has been described above. Next, a detailed operation process of step S620 will be described with reference to FIG. 16.

Figure 16:
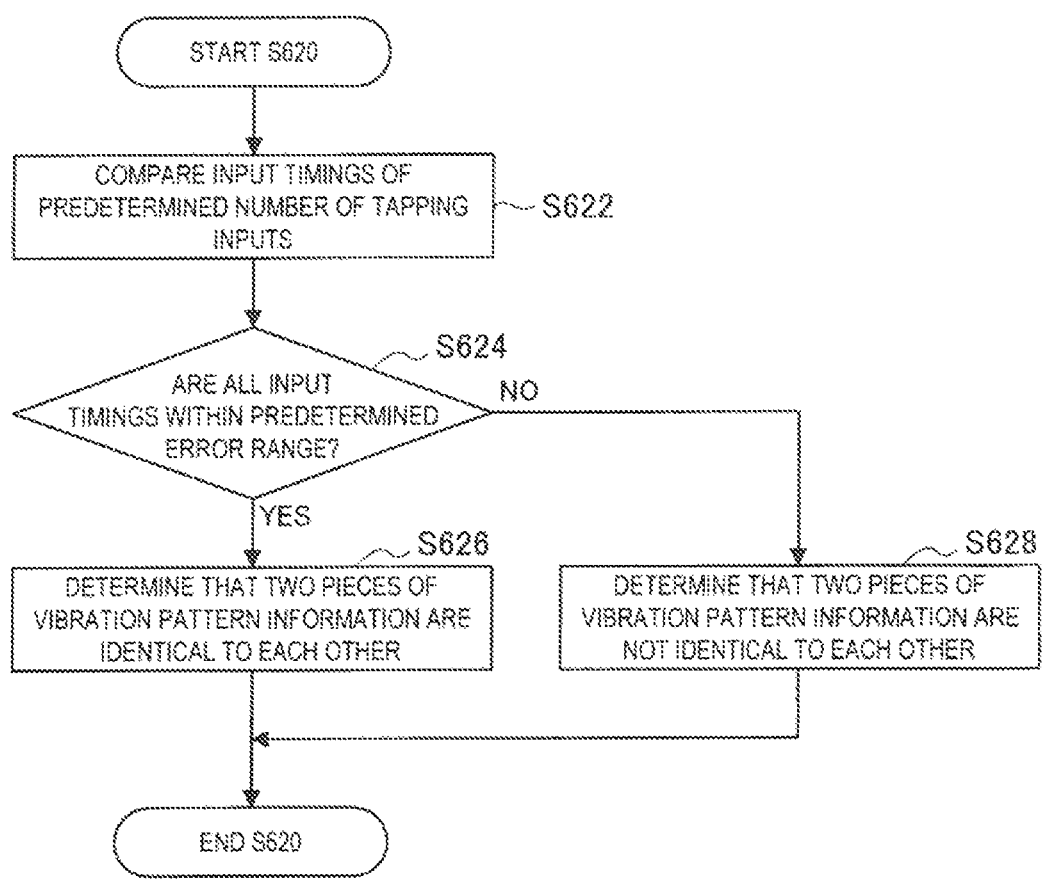
FIG. 16 is a flowchart illustrating an operation of a wristband-type terminal according to the sixth embodiment.

FIG. 16 is a flowchart illustrating an operation of the wristband-type terminal 1-1 according to the sixth embodiment. As illustrated in FIG. 16, first, in step S622, the pattern determining unit 151 compares input timings of a predetermined number of tapping inputs. More specifically, the pattern determining unit 151 compares a predetermined number of timings at which the amplitude has exceeded a predetermined threshold value, that is, a predetermined number of timings at which the users tap the wristband-type terminal 1 with their fingers.

Then, in step S624, the pattern determining unit 151 determines whether or not all the input timings are within a predetermined error range. More specifically, the pattern determining unit 151 determines whether or not a difference between the input timings of the predetermined number of tapping inputs compared in step S622 is within a predetermined error range. Here, the comparison of the vibration pattern information by the pattern determining unit 151 will be described with reference to FIG. 17 using a specific example.

Figure 17:
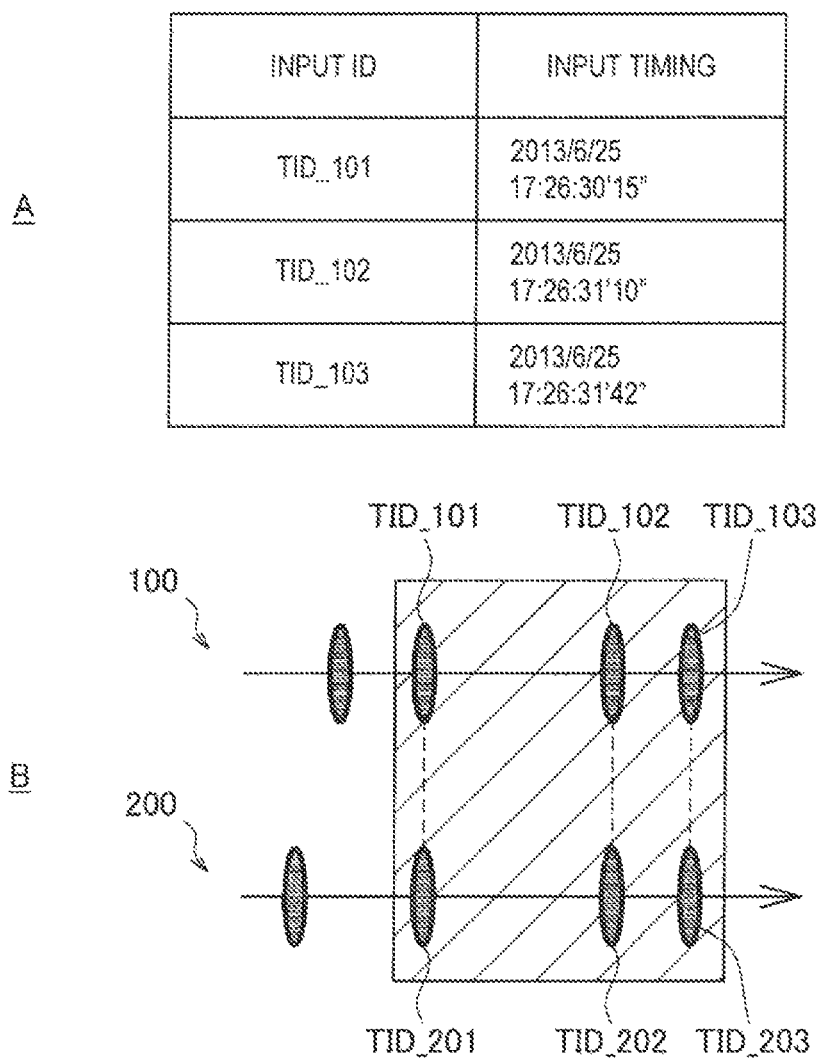
FIG. 17 is a diagram for describing a comparison of vibration pattern information by the wristband-type terminal according to the sixth embodiment.

FIG. 17 is a diagram for describing the comparison of the vibration pattern information by the wristband-type terminal 1-1 according to the sixth embodiment. More specifically, FIG. 17A illustrates a specific example of content of the vibration pattern information. As illustrated in FIG. 17A, the vibration pattern information includes an input ID and an input timing. The input timing refers to an input timing of the tapping input, that is, a timing at which the amplitude when the user taps the wristband-type terminal 1 with his/her finger has exceeded a predetermined threshold value, and the input ID is an ID specific to one input timing.

FIG. 17B illustrates the vibration pattern information (denoted by a reference numeral 100 in FIG. 17B) acquired in the wristband-type terminal 1-1 and the vibration pattern information (denoted by a reference numeral 200 in FIG. 17B) acquired in the wristband-type terminal 1-2. More specifically, timings at which the tapping input is performed on the wristband-type terminals 1-1 and 1-2 are arranged along a time axis. Here, the pattern determining unit 151 is assumed to compare input timings of three tapping inputs. Since the input timings of the three tapping inputs of TID_101 and TID_201, TID_102 and TID_202, and TID_103 and TID_203 are identical to one another as illustrated in FIG. 17B, the pattern determining unit 151 determines that the two pieces of vibration pattern information are identical to each other. The comparison of the vibration pattern information has been described above using the specific example. Next, the description of FIG. 16 will continue.

When all the input timings are determined to be within a predetermined error range (YES in S624), in step S626, the pattern determining unit 151 determines that the two pieces of vibration pattern information are identical to each other. On the other hand, when any one of the input timings is determined not to be within a predetermined error range (NO in S624), in step S628, the pattern determining unit 151 determines that the two pieces of vibration pattern information are not identical to each other.

The operation process of the communication system according to the present embodiment has been described above.

2-2-7. Seventh Embodiment

The present embodiment is a form in which the tapping communication end timing is determined, and a notification of the tapping communication end timing is given to the user. An operation mode of determining and notifying of the tapping communication end timing is also referred to as a "session mode." An operation process of the communication system according to the present embodiment will be described below with reference to FIGS. 18 to 20.

Figure 18:
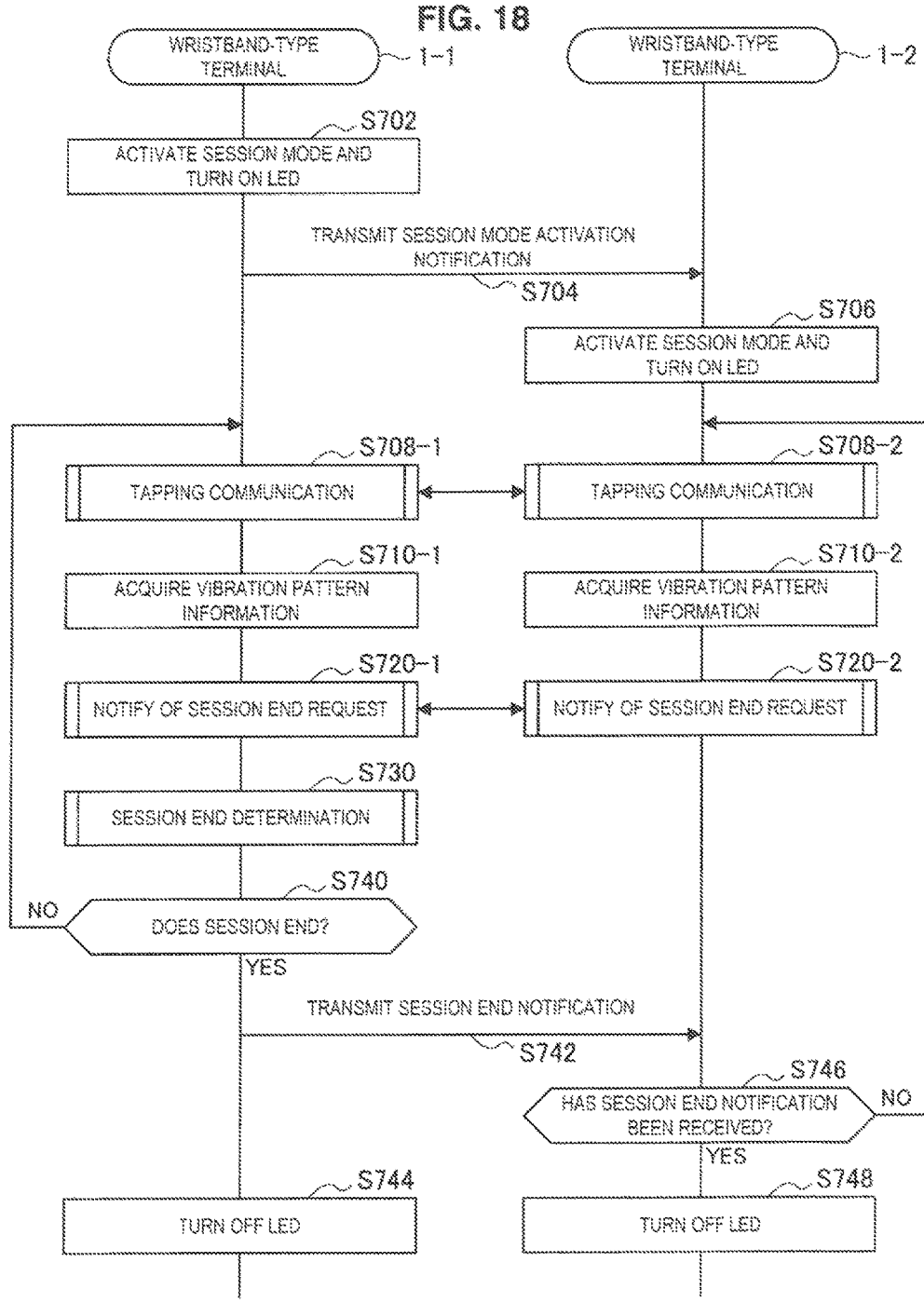
FIG. 18 is a sequence diagram illustrating an operation of a communication system according to a seventh embodiment.

FIG. 18 is a sequence diagram illustrating an operation of the communication system according to a seventh embodiment. As illustrated in FIG. 18, in step S702, the wristband-type terminal 1-1 activates the session mode, and turns on the LED 3 indicating that the wristband-type terminal 1-1 is operating in the session mode.

Then, in step S704, the wristband-type terminal 1-1 transmits a session mode activation notification to the wristband-type terminal 1-2.

Then, in step S706, the wristband-type terminal 1-2 activates the session mode based on the received session mode activation notification, and turns on the LED 3 indicating that the wristband-type terminal 1-2 is operating in the session mode.

Then, in steps S708-1 and S708-2, the wristband-type terminals 1-1 and 1-2 perform the tapping communication. The tapping communication has been described above with reference to FIG. 5, and thus a detailed description thereof is omitted here.

Then, in steps S710-1 and S710-2, the wristband-type terminal 1-1 and the wristband-type terminal 1-2 acquire the vibration pattern information.

Then, in steps S720-1 and S720-2, the wristband-type terminals 1-1 and 1-2 notify of a session end request. This process will be described in detail later with reference to FIG. 19, and thus a description thereof is omitted here.

Then, in step S730, the wristband-type terminal 1-1 performs a session end determination. This process will be described in detail later with reference to FIG. 20, and thus a description thereof is omitted here.

Then, in step S740, the wristband-type terminal 1-1 determines whether or not a session ends. More specifically, the control unit 15 determines whether or not a session ends with reference to a determination result in step S730 which will be described later.

When the session is determined to end (YES in S740), in step S742, the wristband-type terminal 1-1 transmits a session end notification to the wristband-type terminal 1-2. Thereafter, in step S744, the wristband-type terminal 1-1 turns off the LED 3 indicating that the wristband-type terminal 1-1 is operating in the session mode. Further, when the session is determined not to end (NO in S740), the process returns to step S708-1.

Then, in step S746, the wristband-type terminal 1-2 determines whether or not the session end notification has been received.

When the session end notification is determined to have been received (YES in S746), in step S748, the wristband-type terminal 1-2 turns off the LED 3 indicating that the wristband-type terminal 1-2 is operating in the session mode. Further, when the session end notification is determined not to have been received (NO in S746), the process returns to step S708-2.

The operation process of the communication system according to the present embodiment in the session mode has been described above. Next, a detailed operation process of step S720-1 will be described with reference to FIG. 19. An operation of the wristband-type terminal 1-1 in step S720-1 is the same as the operation of the wristband-type terminal 1-2 in S720-2.

Figure 19:
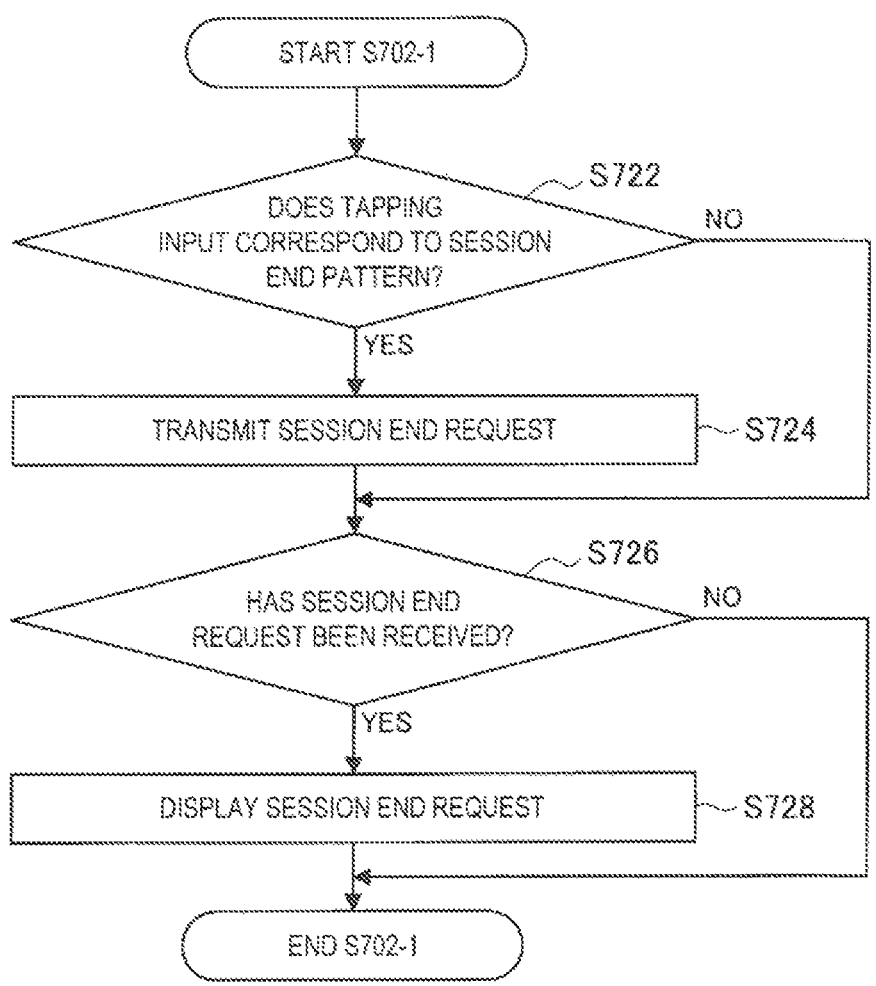
FIG. 19 is a flowchart illustrating an operation of a wristband-type terminal according to the seventh embodiment.
Figure 20:
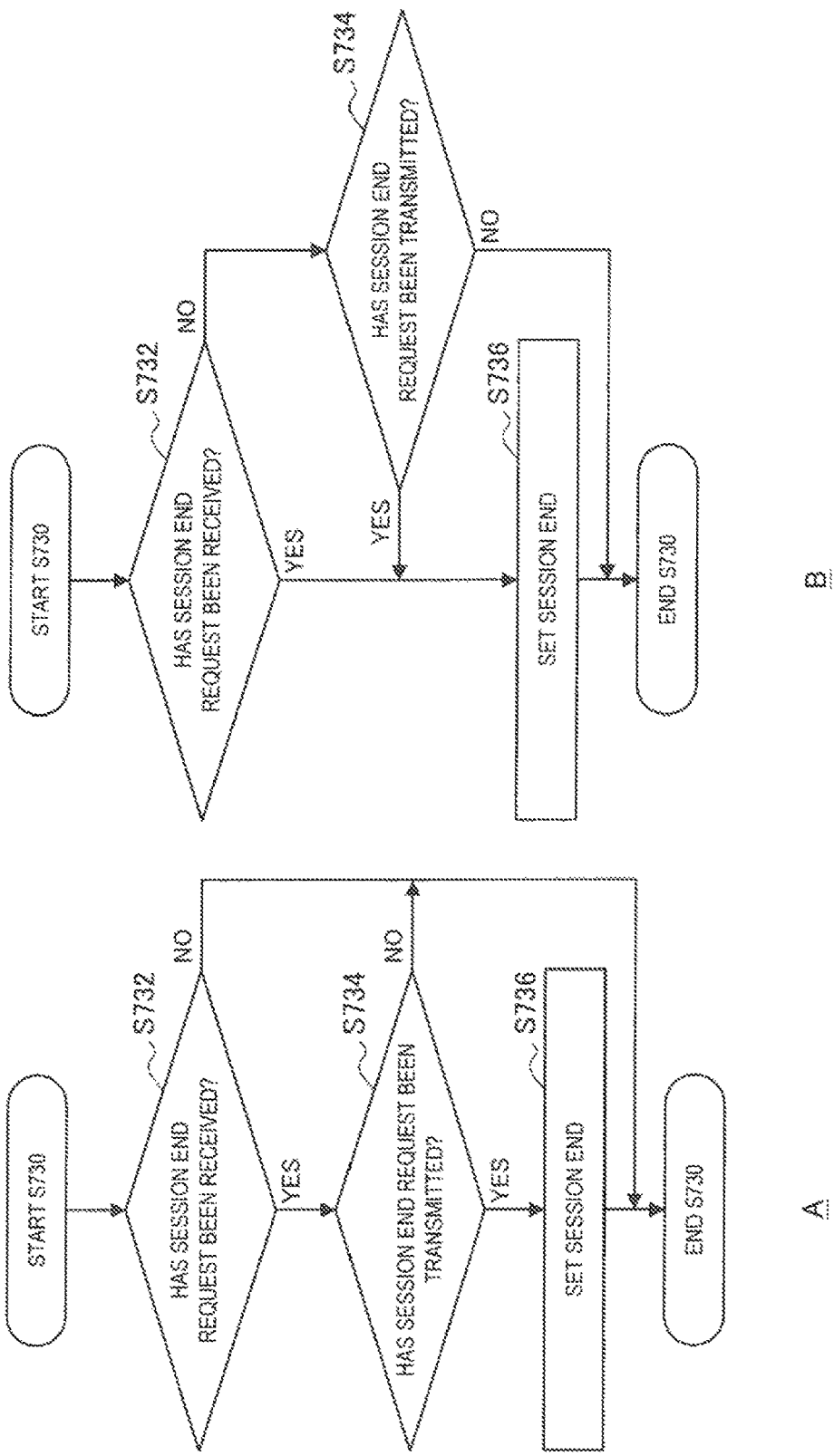
FIGS. 20A and 20B are flowcharts illustrating an operation of the wristband-type terminal according to the seventh embodiment.

FIG. 19 is a flowchart illustrating an operation of the wristband-type terminal 1-1 according to the seventh embodiment. As illustrated in FIG. 19, first, in step S722, the wristband-type terminal 1-1 determines whether or not the tapping input corresponds to a session end pattern. More specifically, the pattern determining unit 151 determines whether or not the vibration pattern by the tapping input is identical to a predetermined vibration pattern indicating an end condition.

When the vibration pattern by the tapping input is determined to be the session end pattern (YES in S722), in step S724, the wristband-type terminal 1-1 transmits the session end request to the wristband-type terminal 1-2. Here, the session end request is a notification for requesting the wristband-type terminal 1-2 to end the session. Specifically, the session end request is a determination result indicating that the tapping input is determined to correspond to the session end pattern. On the other hand, When the vibration pattern by the tapping input is determined not to be the session end pattern (NO in S722), the process proceeds to step S726.

Then, in step S726, the wristband-type terminal 1-1 determines whether or not the session end request has been received from the wristband-type terminal 1-2.

When the session end request is determined to have been received (YES in S726), in step S728, the wristband-type terminal 1-1 displays the session end request. More specifically, the notifying unit 17 gives a notification indicating that the user of the wristband-type terminal 1-2 desires to end the tapping communication through the LED 3 or the display section 5. As a result, the process of step S720-1 ends. Further, when the session end request is determined not to have been received (NO in S726), the process of step S720-1 ends.

The detailed operation process of step S720-1 of FIG. 18 has been described above. Next, a detailed operation process of step S730 of FIG. 18 will be described with reference to FIG. 20.

FIGS. 20A and 20B are flowcharts illustrating an operation of the wristband-type terminal 1-1 according to the seventh embodiment. As the session end determination of step S730, two forms, that is, a form (FIG. 20A) in which the end condition is satisfied when the session end request is mutually transmitted and a form (FIG. 20B) in which the end condition is satisfied when the session end request is transmitted from any one, are considered. The respective forms will be described below.

As illustrated in FIG. 20A, first, in step S732, the wristband-type terminal 1-1 determines whether or not the session end request has been received. More specifically, the control unit 15 determines whether or not the session end request has been received from the wristband-type terminal 1-2 by the communication unit 19 in step S728 (FIG. 19).

When the session end request is determined to have been received (YES in S732), in step S734, the wristband-type terminal 1-1 determines whether or not the session end request has been transmitted. More specifically, the control unit 15 determines whether or not the session end request has been transmitted to the wristband-type terminal 1-2 by the communication unit 19 in step S724 (FIG. 19).

When the session end request is determined to have been transmitted (YES in S734), in step S736, the wristband-type terminal 1-1 sets the session end as the determination result. As a result, the process of step S730 ends.

On the other hand, when the session end request is determined not to have been received (NO in S732), and when the session end request is determined not to have been transmitted (NO in S734), the process of step S730 ends.

The session end determination in which the end condition is satisfied when the session end request is mutually transmitted has been described above. Next, the session end determination in which the end condition is satisfied when the session end request is transmitted from any one will be described.

As illustrated in FIG. 20B, first, in step S732, the wristband-type terminal 1-1 determines whether or not the session end request has been received.

When the session end request is determined to have been received (YES in S732), in step S736, the wristband-type terminal 1-1 sets the session end as the determination result. As a result, the process of step S730 ends.

On the other hand, when the session end request is determined not to have been received (NO in S732), in step S734, the wristband-type terminal 1-1 determines whether or not the session end request has been transmitted.

When the session end request is determined to have been transmitted (YES in S734), in step S736, the wristband-type terminal 1-1 sets the session end as the determination result. As a result, the process of step S730 ends.

On the other hand, when the session end request is determined not to have been transmitted (NO in S734), the process of step S730 ends.

The operation process of the communication system according to the present embodiment has been described above.

2-2-8. Eighth Embodiment

The present embodiment is a form in which an output pattern of vibration, a sound output, or an image output is selected according to a pattern of the tapping input from among sounds or images that are stored in advance. For example, when the other party performs the tapping input according to a specific pattern, a sound such as "how are you?" is output from the wristband-type terminal 1 of the user. The sound may be a synthesized sound or a sound in which a voice of a boyfriend, a girlfriend, or a child is recorded. A form in which an output pattern is selected according to the pattern of the tapping input is also referred to as an "output pattern selection mode." An operation process of the communication system according to the present embodiment will be described below with reference to FIGS. 21 to 24.

Figure 21:
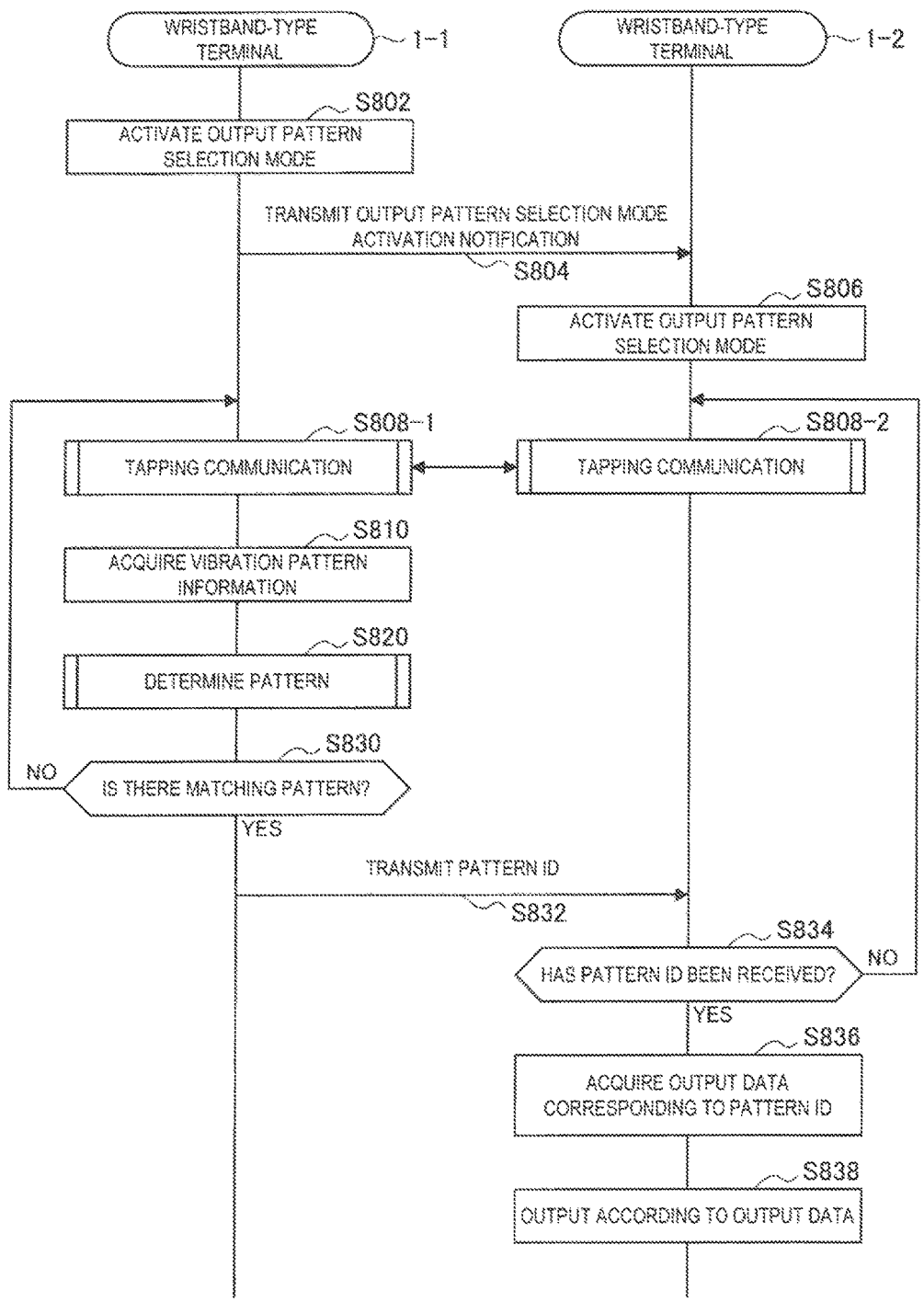
FIG. 21 is a sequence diagram illustrating an operation of a communication system according to an eighth embodiment.

FIG. 21 is a sequence diagram illustrating an operation of the communication system according to an eighth embodiment. As illustrated in FIG. 21, in step S802, the wristband-type terminal 1-1 activates the output pattern selection mode.

Then, in step S804, the wristband-type terminal 1-1 transmits an output pattern selection mode activation notification to the wristband-type terminal 1-2.

Then, in step S806, the wristband-type terminal 1-2 activates the output pattern selection mode based on the received output pattern selection mode activation notification.

Then, in steps S808-1 and S808-2, the wristband-type terminals 1-1 and 1-2 perform the tapping communication. The tapping communication has been described above with reference to FIG. 5, and thus a detailed description thereof is omitted here.

Then, in step S810, the wristband-type terminal 1-1 acquires the vibration pattern information.

Then, in step S820, the wristband-type terminal 1-1 determines whether or not the vibration pattern indicated by the vibration pattern information acquired in step S810 is identical to a previously set vibration pattern. This process will be described in detail later with reference to FIG. 23, and thus a description thereof is omitted.

Then, in step S830, the wristband-type terminal 1-1 determines whether or not there is an identical pattern. More specifically, the control unit 15 determines whether or not there is a pattern identical to the previously set vibration pattern with reference to the determination result obtained by the pattern determining unit 151 in step S820.

When it is determined that there is an identical pattern (YES in S830), in step S832, the wristband-type terminal 1-1 transmits a pattern ID to the wristband-type terminal 1-2. Here, the pattern ID is identical information indicating the pattern determined to be identical in step S820. When it is determined that there is no identical pattern (NO in S830), the process returns to step S808-1.

Then, in step S834, the wristband-type terminal 1-2 determines whether or not the pattern ID has been received.

When the pattern ID is determined to have been received (YES in S834), the wristband-type terminal 1-2 acquires output data corresponding to the received pattern ID. More specifically, the control unit 15 searches for sound data or image data stored in association with the pattern ID from the storage unit 18. Further, when the pattern ID is determined not to have been received (NO in S834), the process returns to step S808-2.

Then, in step S838, the wristband-type terminal 1-2 performs an output according to the output data. More specifically, the vibrating unit 16 or the notifying unit 17 performs vibration, a sound output, or an image display according to the output data that is acquired in step S836 and corresponds to the received pattern ID. An output of the wristband-type terminal 1-2 will be described with reference to FIG. 22 using a specific example.

FIG. 22 is a diagram for describing output pattern selection by the wristband-type terminal 1-1 according to the eighth embodiment. As illustrated in FIG. 22, the pattern IDs are associated with the vibration pattern, the sound data, and the image data. For example, when the received pattern ID is PID_001, the wristband-type terminal 1-2 vibrates the vibrating unit 16 according to a vibration pattern Vib_012. Further, when the received pattern ID is PID_002, the wristband-type terminal 1-2 causes the vibrating unit 16 to vibrate according to a vibration pattern Vib_105 and causes the notifying unit 17 to reproduce sound data Aud_023 and display image data Img_041. Further, when the received pattern ID is PID_003, the wristband-type terminal 1-2 causes the vibrating unit 16 to vibrate according to a vibration pattern Vib_003 and causes the notifying unit 17 to display image data Img_005.

The operation process of the communication system according to the present embodiment in the output pattern selection mode has been described above. Next, a detailed operation process of step S820 will be described with reference to FIG. 23.

Figure 23:
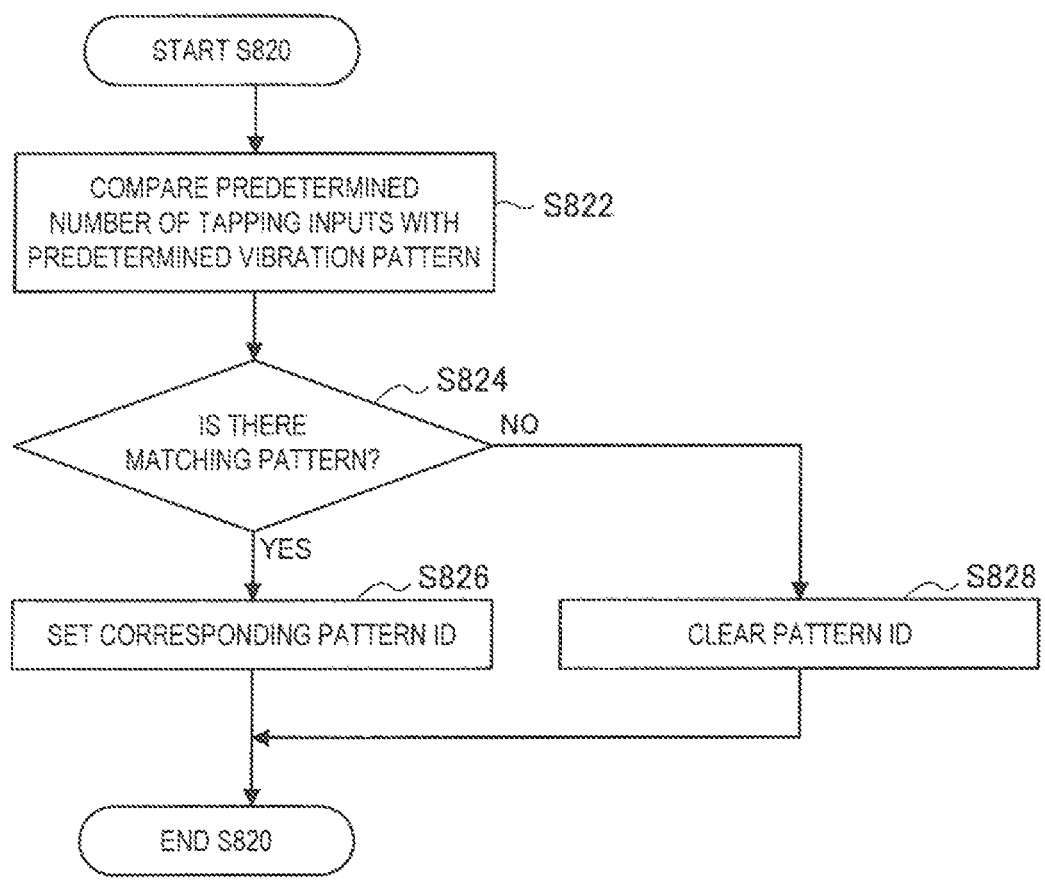
FIG. 23 is a flowchart illustrating an operation of the wristband-type terminal according to the eighth embodiment.

FIG. 23 is a flowchart illustrating an operation of the wristband-type terminal 1-1 according to the eighth embodiment. As illustrated in FIG. 23, first, in step S822, the pattern determining unit 151 compares a predetermined number of tapping inputs with a predetermined vibration pattern. More specifically, the pattern determining unit 151 compares a rhythm in which the amplitude has exceeded a predetermined threshold value, that is, a rhythm in which the user taps the wristband-type terminal 1 with his/her finger with a rhythm indicated by a previously set vibration pattern.

Then, in step S824, the wristband-type terminal 1-1 determines whether or not there is a pattern that matches a predetermined number of tapping inputs. More specifically, the pattern determining unit 151 determines whether or not a rhythm of the tapping input is identical to a rhythm indicated by a previously set vibration pattern.

When it is determined that there is a matching pattern (YES in S824), in step S826, the wristband-type terminal 1-1 sets a corresponding pattern ID. Here, a specific example of setting a corresponding pattern ID through the wristband-type terminal 1-1 will be described with reference to FIG. 24.

FIG. 24 is a diagram for describing a setting of the pattern ID in the wristband-type terminal 1-1 according to the eighth embodiment. For example, when the rhythm of the tapping input is identical to a vibration pattern Pat_Tap_001, the pattern determining unit 151 sets PID_001 as the pattern ID. Further, when the rhythm of the tapping input is identical to a vibration pattern Pat_Tap_002, the pattern determining unit 151 sets PID_002 as the pattern ID. Furthermore, when the rhythm of the tapping input is identical to a vibration pattern Pat_Tap_003, the pattern determining unit 151 sets PID_003 as the pattern ID. The setting of the pattern ID has been described above using the specific example. Next, the description of FIG. 23 will continue.

On the other hand, when it is determined that there is no matching pattern (NO in S824), in step S828, the wristband-type terminal 1-1 clears the pattern ID.

The operation process of the communication system according to the present embodiment has been described above.

3. CONCLUSION

As described above, the communication system according to an embodiment of the present disclosure can implement more casual intimate communication. More specifically, the communication system according to the embodiments of the present disclosure can enable communication of exchanging greetings to be performed with a specific person frequently without reluctance.

Although preferred embodiments of the present disclosure have been described in detail above with reference to the appended drawings, the technical scope of the embodiments of the present disclosure is not limited to the above example. It is obvious to those with a general knowledge of the technical field of the embodiments of the present disclosure that various modifications and alterations may occur within the technical scope defined in the claims, and that these modifications and alterations are encompassed within the technical scope of the embodiments of the present disclosure.

For example, it is also possible to create a computer program that causes hardware such as a CPU, a ROM, and a RAM built in an information processing device to perform the same functions as the respective components of the wristband-type terminal 1. Further, a recording medium on which the computer program is recorded is also provided.

Furthermore, the advantages discussed in this specification are only intended for illustrative and exemplary purposes and are not limitative. In other words, in addition to or in place of the above-described advantages, the technology according to the embodiments of the present disclosure may exhibit other advantages that are obvious to a skilled person from the specification.

Additionally, the present technology may also be configured as below.

(1)

A wristband-type information processing device including:
    a band section configured to be worn on a wrist of a user;
    a sensor unit configured to detect a motion of the user;
    a vibration signal generating unit configured to generate a first vibration signal for vibrating another associated wristband-type information processing device according to the motion detected by the sensor unit; and
    a communication unit configured to transmit the first vibration signal generated by the vibration signal generating unit to the other wristband-type information processing device.

(2)

The wristband-type information processing device according to (1), further including
    a state signal generating unit,
    wherein the sensor unit detects a state of the user, the state signal generating unit generates a first state signal for notifying another user wearing the other wristband-type information processing device of the state of the user detected by the sensor unit, and the communication unit transmits the first state signal to the other wristband-type information processing device.

(3)

The wristband-type information processing device according to (2), further including a notifying unit, wherein, when the communication unit receives a second state signal generated according to a state of the other user from the other wristband-type information processing device, the notifying unit notifies the user of information indicating the state of the other user according to the second state signal.

(4)

The wristband-type information processing device according to (3), wherein, when the communication unit receives a second vibration signal generated according to a motion of the other user from the other wristband-type information processing device after the communication unit transmits the first state signal, the notifying unit notifies the user of information indicating the state of the user.

(5)

The wristband-type information processing device according to any one of (1) to (5), further including a motion determining unit configured to determine whether or not the motion detected by the sensor unit is a predetermined motion, wherein the vibration signal generating unit generates the first vibration signal when the motion determining unit determines that the motion of the user is the predetermined motion.

(6)

The wristband-type information processing device according to (5), wherein the predetermined motion is a motion in which the user taps the wristband-type information processing device, and the motion determining unit determines whether or not the motion of the user is the predetermined motion based on vibration detected by the sensor unit.

(7)

The wristband-type information processing device according to any one of (1) to (6), further including a vibrating unit, wherein, when the communication unit receives a second vibration signal generated according to a motion of the other user from the other wristband-type information processing device, the vibrating unit vibrates according to the second vibration signal.

(8)

The wristband-type information processing device according to (7), wherein the vibrating unit vibrates according to a predetermined vibration pattern when the communication unit receives the second vibration signal.

(9)

The wristband-type information processing device according to (7) or (8), further including a storage unit configured to store a state of the user detected by the sensor unit, wherein the vibrating unit vibrates when a state identical or similar to the state of the user stored in the storage unit is detected by the sensor unit.

(10)

The wristband-type information processing device according to any one of (1) to (10), further including a notifying unit, wherein the sensor unit detects whether or not the user is wearing the wristband-type information processing device, and the notifying unit notifies the user of information indicating that the second vibration signal has been received when the second vibration signal has been received by the communication unit but the sensor unit detects that the user is not wearing the wristband-type information processing device.

(11)

The wristband-type information processing device according to any one of (1) to (10), further including a vibration pattern generating unit configured to generate first vibration pattern information indicating a vibration pattern detected by the sensor unit, wherein the communication unit receives second vibration pattern information generated in the other wristband-type information processing device.

(12)

The wristband-type information processing device according to (11), further including:

a notifying unit; and a first pattern determining unit configured to determine whether or not a vibration pattern indicated by the first vibration pattern information is identical to a vibration pattern indicated by the second vibration pattern information, wherein the notifying unit notifies the user of a determination result obtained by the first pattern determining unit.

(13)

The wristband-type information processing device according to (11) or (12), further including:

a notifying unit; and a second pattern determining unit configured to determine whether or not a vibration pattern indicated by the first vibration pattern information is identical to a third vibration pattern, wherein the communication unit transmits a determination result obtained by the second pattern determining unit to the other wristband-type information processing device to notify the other user of the determination result.

(14)

The wristband-type information processing device according to any one of (11) to (13), further including a third pattern determining unit configured to determine whether or not a vibration pattern indicated by the first vibration pattern information is identical to a fourth vibration pattern, wherein the communication unit transmits a determination result obtained by the third pattern determining unit to the other wristband-type information processing device to cause the other wristband-type information processing device to output an output corresponding to the determination result.

(15)

The wristband-type information processing device according to any one of (1) to (14), further including a setting unit configured to perform a setting for associating with another wristband-type information processing device different from the other wristband-type information processing device.

(16)

An information processing system including:

a first wristband-type information processing device; and a second wristband-type information processing device associated with the first wristband-type information processing device,
  wherein the first wristband-type information processing device includes
    a band section configured to be worn on a wrist of a first user,
    a sensor unit configured to detect a motion of the first user,
    a vibration signal generating unit configured to generate a first vibration signal for vibrating the associated second wristband-type information processing device, and
    a communication unit configured to transmit the first vibration signal generated by the vibration signal generating unit to the second wristband-type information processing device, and
  the second wristband-type information processing device includes
    a band section configured to be worn on a wrist of a second user,
    a communication unit configured to receive the first vibration signal from the first wristband-type information processing device, and
    a vibrating unit configured to vibrate according to the first vibration signal received by the communication unit.
(17)
An information processing method including:
detecting a motion of a user wearing a band section;
generating a first vibration signal for vibrating another associated wristband-type information processing device according to the detected motion; and
transmitting the generated first vibration signal to the other wristband-type information processing device.
(18)
A program causing a computer to function as:
a sensor unit configured to detect a motion of a user wearing a band section;
a vibration signal generating unit configured to generate a first vibration signal for vibrating another associated wristband-type information processing device according to the motion detected by the sensor unit; and
a communication unit configured to transmit the first vibration signal generated by the vibration signal generating unit to the other wristband-type information processing device.
(19)
A storage medium that stores a program causing a computer to function as:
a sensor unit configured to detect a motion of a user wearing a band section;
a vibration signal generating unit configured to generate a first vibration signal for vibrating another associated wristband-type information processing device according to the motion detected by the sensor unit; and
a communication unit configured to transmit the first vibration signal generated by the vibration signal generating unit to the other wristband-type information processing device.

REFERENCE SIGNS LIST 1, 1-1, 1-2 wristband-type terminal
11 I/F
12 setting unit
13 sensor unit
14 A/D converting unit
15 control unit
151 pattern determining unit
152 motion determining unit
153 state determining unit
154 vibration pattern generating unit
155 state signal generating unit
156 vibration signal generating unit
16 vibrating unit
17 notifying unit
18 storage unit
19 communication unit
2 clock
3 LED
4 band section
5 display section
6 avatar
7 network
9 user

The invention claimed is:
1. A first wristband information processing device, comprising:
  a sensor unit configured to detect an input motion of a first user associated with the first wristband information processing device;
  a storage unit configured to store a plurality of states;
  a state determining unit configured to determine a first state of the first user based on the detected input motion of the first user;
  a vibration signal information generating unit configured to generate first vibration signal information to vibrate a second wristband information processing device,
    wherein the first vibration signal information is generated based on the detected input motion of the first user;
  a communication unit configured to:
  transmit the determined first state of the first user and the first vibration signal information to the second wristband information processing device; and
  receive second vibration signal information, generated based on an input motion of a second user, from the second wristband information processing device; and
  a vibrating unit configured to vibrate the first wristband information processing device based on the second vibration signal information and based on the first state that is identical to one of the plurality of states stored in the storage unit.
2. The first wristband information processing device according to claim 1, further comprising a state signal generating unit configured to generate a first state signal to notify a second user of the determined first state of the first user, wherein
  the second user is associated with the second wristband information processing device, and
  the communication unit is further configured to transmit the first state signal to the second wristband information processing device.
3. The first wristband information processing device according to claim 2, further comprising a notifying unit configured to notify the first user of a second state of the second user based on a second state signal,
  wherein the second state signal is generated based on the second state of the second user, and
  wherein the communication unit is further configured to receive the second state signal from the second wristband information processing device.
4. The first wristband information processing device according to claim 3, wherein the communication unit is further configured to receive the second vibration signal information subsequent to the transmission of the first state signal, and wherein the notifying unit is further configured to notify the first user of the second state of the second user based on the reception of the second vibration signal information.

5. The first wristband information processing device according to claim 1, wherein the vibration signal information generating unit is further configured to generate the first vibration signal information based on a determination that the detected input motion of the first user is a specific motion for which information is saved in the first wristband information processing device.

6. The first wristband information processing device according to claim 1, wherein the detected input motion of the first user is a motion in which the first user taps the first wristband information processing device.

7. The first wristband information processing device according to claim 1, wherein the vibrating unit is further configured to vibrate based on a vibration pattern, based on the second vibration signal information.

8. The first wristband information processing device according to claim 1, wherein the storage unit is further configured to store the first state of the first user detected by the sensor unit.

9. The first wristband information processing device according to claim 1, further comprising a notifying unit configured to notify the first user of information to indicate a receipt of the second vibration signal information by the communication unit and a failure, at a time of the receipt, of the sensor unit to detect the first wristband information processing device on a wrist of the first user.

10. The first wristband information processing device according to claim 1, further comprising a vibration pattern generating unit configured to generate first vibration pattern information to indicate a first vibration pattern detected by the sensor unit, wherein the communication unit is further configured to receive second vibration pattern information generated in the second wristband information processing device.

11. The first wristband information processing device according to claim 10, further comprising:

a first pattern determining unit configured to determine the first vibration pattern indicated by the first vibration pattern information is identical to a second vibration pattern indicated by the second vibration pattern information; and a notifying unit configured to notify the first user of a determination result obtained by the first pattern determining unit.

12. The first wristband information processing device according to claim 10, further comprising a second pattern determining unit configured to determine the first vibration pattern indicated by the first vibration pattern information is identical to a third vibration pattern, wherein the communication unit is further configured to transmit a determination result obtained by the second pattern determining unit to the second wristband information processing device to notify the second user of the determination result.

13. The first wristband information processing device according to claim 10, further comprising a third pattern determining unit configured to determine the first vibration pattern indicated by the first vibration pattern information is identical to a fourth vibration pattern, wherein the communication unit is further configured to transmit a determination result obtained by the third pattern determining unit to the second wristband information processing device, and wherein the second wristband information processing device transmits an output based on the determination result.

14. The first wristband information processing device according to claim 1, further comprising a setting unit configured to associate the first wristband information processing device with a plurality of second wristband information processing devices.

15. An information processing system, comprising:

a first wristband information processing device; and a second wristband information processing device associated with the first wristband information processing device, wherein the first wristband information processing device includes:

a sensor unit configured to detect an input motion of a user associated with the first wristband information processing device, a storage unit configured to store a plurality of states, a state determining unit configured to determine a state of the user based on the detected input motion of the user, a vibration signal information generating unit configured to generate first vibration signal information to vibrate the second wristband information processing device, wherein the first vibration signal information is generated based on the detected input motion of the user, a first communication unit configured to transmit the determined state of the user and the first vibration signal information to the second wristband information processing device, and a first vibrating unit, and wherein the second wristband information processing device includes:

a second communication unit configured to:

receive the first vibration signal information from the first wristband information processing device, and transmit second vibration signal information to the first wristband information processing device, and a second vibrating unit configured to vibrate the second wristband information processing device based on the first vibration signal information received by the second communication unit, wherein the first vibrating unit is configured to vibrate the first wristband information processing device based on the second vibration signal information and based on the state that is identical to one of the plurality of states stored in the storage unit.

16. An information processing method, comprising:

detecting an input motion of a first user associated with a first wristband information processing device;

storing a plurality of states;

determining a state of the first user based on the detected input motion of the first user;

generating first vibration signal information for vibrating a second wristband information processing device, wherein the first vibration signal information is generated based on the detected input motion;

transmitting the determined state of the first user and the generated first vibration signal information to the second wristband information processing device;

receiving second vibration signal information, generated based on an input motion of a second user, from the second wristband information processing device; and vibrating the first wristband information processing device based on the second vibration signal information and based on the state that is identical to one of the plurality of states.

17. A non-transitory computer-readable medium having stored thereon computer-executable instructions that, when executed by a processor, cause a computer to execute operations, the operations comprising:

detecting an input motion of a first user associated with a first wristband information processing device;

storing a plurality of states;

determining a state of the first user based on the detected input motion of the first user;

generating first vibration signal information for vibrating a second wristband information processing device, wherein the first vibration signal information is generated based on the detected input motion of the first user;

transmitting the determined state of the first user and the generated first vibration signal information to the second wristband information processing device;

receiving second vibration signal information, generated based on an input motion of a second user, from the second wristband information processing device; and vibrating the first wristband information processing device based on the second vibration signal information and based on the state that is identical to one of the plurality of states.

* * * * *